US011576999B2

(12) United States Patent
Francis et al.

(10) Patent No.: US 11,576,999 B2
(45) Date of Patent: Feb. 14, 2023

(54) COMPRESSED BONE COMPOSITION AND METHODS OF USE THEREOF

(71) Applicant: LifeNet Health, Virginia Beach, VA (US)

(72) Inventors: Michael Francis, Virginia Beach, VA (US); Rudy Rodriquez, Virginia Beach, VA (US); Nathan Kemper, Virginia Beach, VA (US); Silvia Chen, Kendall Park, NJ (US)

(73) Assignee: LifeNet Health, Virginia Beach, VA (US)

( * ) Notice: Subject to any disclaimer, the term of this patent is extended or adjusted under 35 U.S.C. 154(b) by 348 days.

(21) Appl. No.: 16/988,078

(22) Filed: Aug. 7, 2020

(65) Prior Publication Data
US 2020/0368391 A1 Nov. 26, 2020

Related U.S. Application Data

(62) Division of application No. 15/028,639, filed as application No. PCT/US2014/059980 on Oct. 9, 2014, now Pat. No. 10,780,196.

(60) Provisional application No. 62/045,929, filed on Sep. 4, 2014, provisional application No. 61/889,010, filed on Oct. 9, 2013.

(51) Int. Cl.
*A61L 27/36* (2006.01)
*A61L 27/56* (2006.01)
*A61L 27/38* (2006.01)
*A61L 27/50* (2006.01)
*A61F 2/28* (2006.01)
*B28B 1/00* (2006.01)
(Continued)

(52) U.S. Cl.
CPC ............ *A61L 27/3608* (2013.01); *A61F 2/28* (2013.01); *A61L 27/365* (2013.01); *A61L 27/3834* (2013.01); *A61L 27/502* (2013.01); *A61L 27/56* (2013.01); *B28B 1/007* (2013.01); *B28B 17/02* (2013.01); *A61F 2002/2817* (2013.01); *A61F 2002/2828* (2013.01); *A61L 2430/02* (2013.01); *B33Y 80/00* (2014.12)

(58) Field of Classification Search
CPC combination set(s) only.
See application file for complete search history.

(56) References Cited

U.S. PATENT DOCUMENTS 5,549,697 A 8/1996 Caldarise
5,556,379 A 9/1996 Wolfinbarger, Jr.
(Continued)

FOREIGN PATENT DOCUMENTS

WO 0050102 A1 8/2000
WO 2007139949 A2 12/2007

OTHER PUBLICATIONS

Canadian Examination Report for Canadian Application No. 2,925,584, dated Jul. 26, 2021, 3 pages.
Canadian Examination Report for Canadian Application No. 2,925,584 dated Nov. 20, 2020, 7 pages.
(Continued)

*Primary Examiner* — Sameh R Boles
(74) *Attorney, Agent, or Firm* — RatnerPrestia

(57) ABSTRACT

The present disclosure relates to compressed bone compositions, bone implants, and variants thereof. The present disclosure also relates to methods of preparing compressed bone compositions, bone implants, and variants thereof. The present disclosure also relates to methods of using the bone compositions, bone implants and variants thereof.

16 Claims, 13 Drawing Sheets

(51) Int. Cl.
*B28B 17/02* (2006.01)
*B33Y 80/00* (2015.01)

(56) References Cited

U.S. PATENT DOCUMENTS

| | | | |
|---|---|---|---|
| 5,797,871 | A | 8/1998 | Wolfinbarger, Jr. |
| 5,820,581 | A | 10/1998 | Wolfinbarger, Jr. |
| 5,977,034 | A | 11/1999 | Wolfinbarger, Jr. |
| 5,977,432 | A | 11/1999 | Wolfinbarger, Jr. et al. |
| 6,293,970 | B1 | 9/2001 | Wolfinbarger, Jr. et al. |
| 6,440,444 | B2 | 8/2002 | Boyce et al. |
| 7,001,551 | B2 | 2/2006 | Meredith |
| 7,063,726 | B2 | 6/2006 | Crouch et al. |
| 7,744,597 | B2 | 6/2010 | Gaskins et al. |
| 8,246,680 | B2 | 8/2012 | Betz et al. |
| 2003/0036800 | A1 | 2/2003 | Meredith |
| 2004/0059364 | A1 | 3/2004 | Gaskins et al. |
| 2010/0030340 | A1 | 2/2010 | Wolfinbarger, Jr. et al. |
| 2010/0185284 | A1 | 7/2010 | Crouch et al. |
| 2012/0273993 | A1 | 11/2012 | Shoseyov et al. |
| 2013/0189338 | A1 | 7/2013 | Drapeau et al. |
| 2015/0283182 | A1* | 10/2015 | Guelcher ............... A61K 35/32 424/549 |

OTHER PUBLICATIONS

Korean Notice to File a Response in Korean Application No. 10-2016-7011468, dated Feb. 22, 2021, with translation, 19 pages.
European Communication Pursuant to Article 94(3) for European Application No. 14852726.0, dated Apr. 24, 2020, 7 pages.
European Communication Pursuant to Article 94(3) for European Application No. 14 852 726.0, dated Feb. 13, 2019, 6 pages.
International Search Report and Written Opinion of the International Search Authority for International Application No. PCT/US2014/059980, dated Jan. 14, 2015, 9 pages.
International Preliminary Report on Patentabilitiy for International Application No. PCT/US2014/059980, dated Apr. 12, 2016, 7 pages.
Behravesh et al., "Synthetic Biodegradable Polymers for Orthopaidic Applications", Clinical Orthopaedics, vol. 367, Abstract Only, 1 page.
Lu et al., "Polymeric delivery vehicles for bone growth factors: Designing Technologies for the Future, Park and Mrsny eds.", American Chemical Society, vol. 40, 2000, 3 pages.
Anderson et al., "Biodegradation and biocompatibility of PLA and PLGA microspheres", Advanced Drug Delivery Reviews, 1997, Abstract Only, 2 pages.
Cleek et al., "Microparticles of poly(DL-lactic-co-glycolic acid)/poly(ethylene glycol) blends for cnotrolled drug delivery", Journal of Controlled Release, 1997, vol. 48, Issues 2-3, Abstract Only, 2 pages.
Australian Examination Report No. 2 for Australian Application No. 2014331769, dated Sep. 3, 2018, 4 pages.
Australian Examination Report for Australian Application No. 2014331769, dated Jun. 6, 2018, 5 pages.
Extended European Search Report for European Application No. 14852726.0, dated Jun. 20, 2017, 6 pages.
Entire patent prosecution history of U.S. Appl. No. 15/028,639, filed Apr. 11, 2016, entitled "Compressed Bone Composition and Methods of Use Thereof ."

* cited by examiner

| Mag. | SEM Analysis of Dry Samples | | |
|---|---|---|---|
| | CNC 0.003 Chipload<br><br>Bubble Wrap at 900 psi for 20 minutes | CNC 0.009 Chipload<br><br>Bubble Wrap at 900 psi for 20 minutes | Shaver<br><br>Bubble Wrap at 900 psi for 20 minutes |
| X 30 |  |  |  |
| X 250 |  |  |  |
| X $10^3$ |  |  |  |
| X 3000 |  |  |  |

COMPRESSED BONE COMPOSITION AND METHODS OF USE THEREOF

RELATED APPLICATIONS

This application is a divisional of U.S. patent Ser. No. 15/028,639, filed Apr. 11, 2016, now allowed, which is a U.S. National Phase Application of PCT International Application PCT/US2014/059980; filed Oct. 9, 2014, which claims priority to U.S. Provisional Application Nos. 62/045,929, filed Sep. 4, 2014, and 61/889,010 filed Oct. 9, 2013, respectively, each of which is incorporated herein in its entirety for all purposes.

BACKGROUND OF THE INVENTION

The invention relates to methods of preparing compressed bone compositions, bone implants, and variants thereof. The invention also relates to methods of using the bone implants and variants thereof.

The invention relates to compressed bone compositions, particles, fibers, implants, and variants thereof, and the methods of preparing and making the same. The invention also relates to methods of using the bone compositions, particles, fibers, implants, and variants thereof.

Demineralized cortical and cancellous bone compositions have been widely used in the induction of new bone formation for the treatment of a variety of clinical pathologies. Typically, bone materials are obtained from human or animal sources, processed, demineralized, and made into bone implants. Such bone implants may comprise bone compositions which may include for example compressed bone fibers and/or bone fibers. The bone implants may also comprise growth factors, proteins, cells, and other bioactive materials that may facilitate osteoinduction and bone healing. In general, it is desirable to develop new bone materials that have superior wet and dry handling characteristics for processing, and to provide an environment for the attachment and functioning of bioactive molecules.

SUMMARY

The invention relates to methods of preparing compressed bone compositions comprising loading bone particles and/or fibers into a mold with a predetermined shape, applying pressure to the particles and/or fibers, and freeze drying the compressed bone particles and/or fibers. In one aspect, the pressure may be from 0.1 to 30 MPa. In another aspect, the predetermined shape comprises grooves. In another aspect, the compressed bone compositions retain their integrity in liquid for at least 5-30 minutes after being introduced into liquids. In another aspect, pressure is applied to the bone particles and/or fibers at room temperature. In another aspect, the compressed bone compositions do not comprise a binder or a chemical cross-linker.

The invention also relates to bone implants prepared by the methods described herein. In one aspect, the bone implants comprise grooves.

The invention relates to a bone composition comprising bone fibers, wherein the bone fibers comprise microfibers having an average width (W) of less than about 5 µm and an average length (L):W ratio of greater than about 2.

The invention also related to a method for preparing an individualized bone implant, comprising: loading bone composition into a mold that is based upon three dimensional (3D) medical imaging measurements taken from a bone structure of the individual for the implant or prosthesis, wherein the bone composition comprises microfibers having an average length (L): average width (W) ratio greater than about 2; applying pressure of from 0.1 to 30 MPa to the bone composition to fit the mold; and freeze drying the compressed bone composition to make the bone implant. In some embodiments, the measurements are converted to computer aided designs to generate custom molds for compressing the bone fibers.

The invention also relates to bone implants prepared by the methods described herein and the method to use such bone implants.

DETAILED DESCRIPTION OF THE INVENTION

Figure 1:
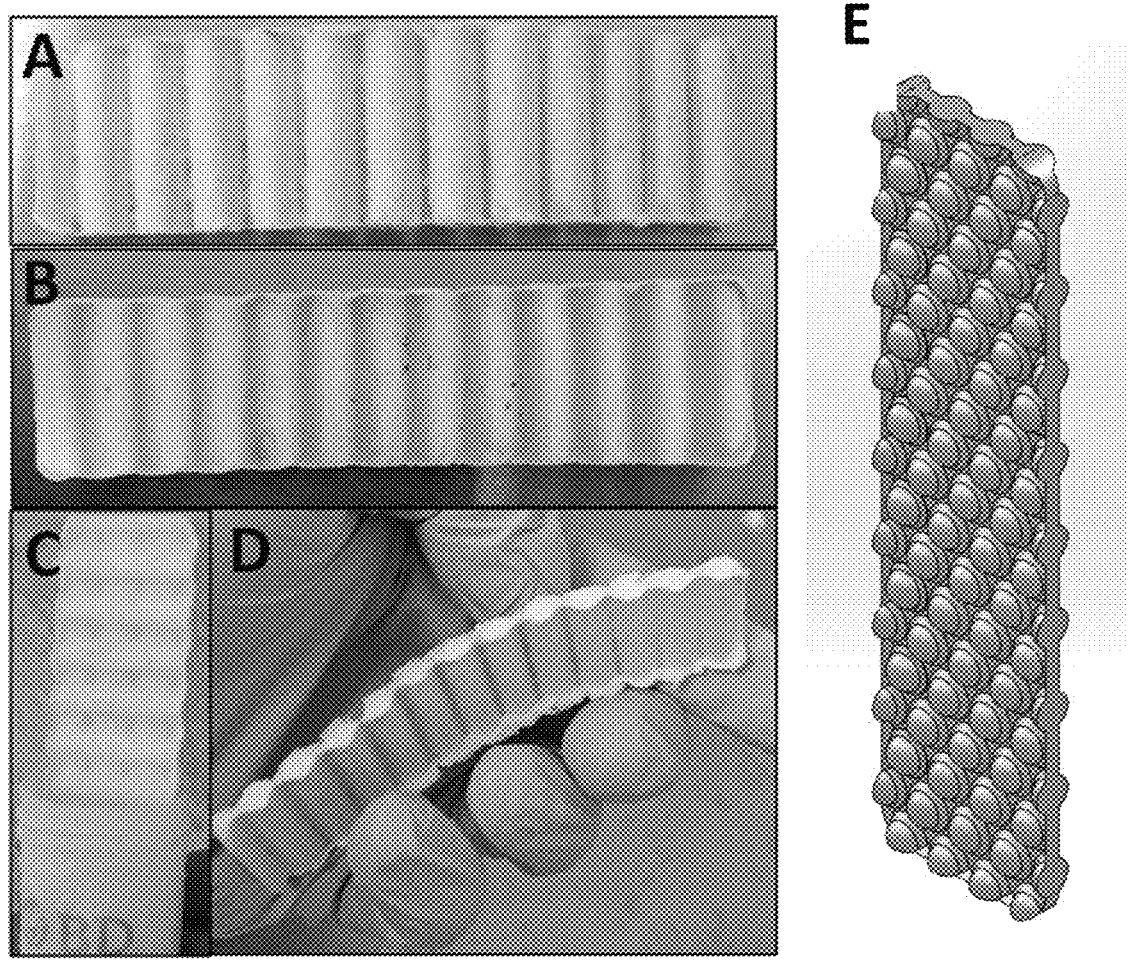
FIG. 1 depicts a mirrored wave (A,D) and single wave (B) structures of compressed bone fibers after lyophilization. A bi-axial wave structure as frozen at −80° C. before the lyophilization is also shown (C). The inherent flexibility of the compressed bone fibers is also depicted (D). A design for the bubble-based graft for increased flexibility is also shown (E).
Figure 2:
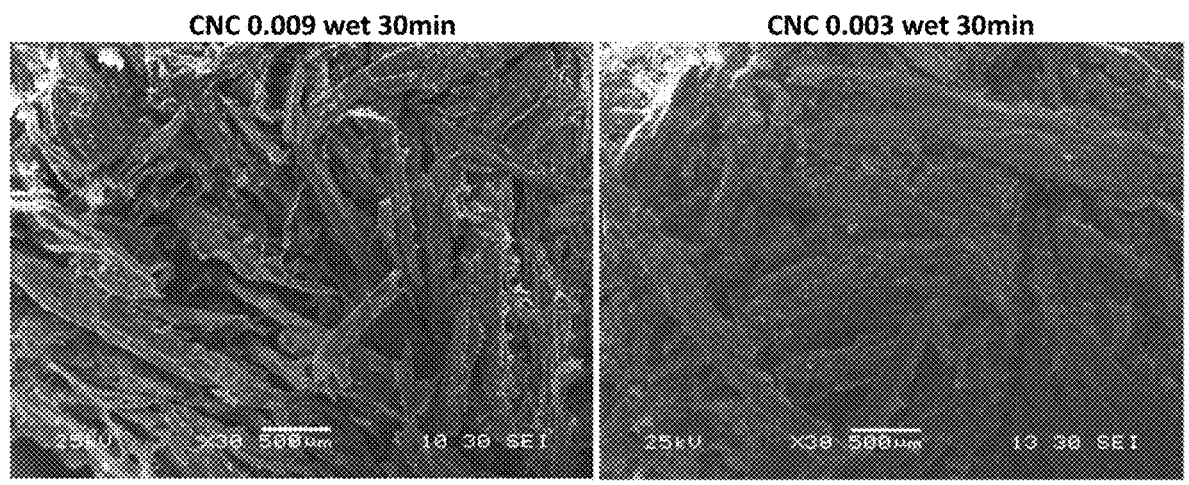
FIG. 2 illustrates samples of bone fibers wetted and thus expanded by hydration in saline for 30 minutes with scanning electron microscope (SEM) according to some embodiments of the present invention.

The invention relates to methods of preparing compressed bone compositions comprising loading bone particles and/or fibers into a mold with a predetermined shape, applying pressure to the bone particles and/or fibers, and freeze drying the compressed bone particles and/or fiber.

The invention also relates to a compressed bone composition comprising bone fibers, wherein the bone fibers comprise microfibers having an average width (W) of less than about 5 μm and an average length (L):W ratio of greater than about 2.

The bone particles described herein include but are not limited to bone fibers and/or powders. The bone fibers described herein include but are not limited to bone fibers and/or powders. Bone particles and/or fibers may be prepared from cleaned and disinfected bone fragments that have or have not been freeze-dried, grounded/fractured, and cut into bone particles and/or fibers. In some embodiments, the bone particles and/or fibers are wetted and pre-freeze dried. Bone particles and/or fibers may be selected by, for example, using sieving devices (e.g. mesh sieves) commercially available to obtain particles and/or fibers within a desired size range. In some embodiments, the fibers are not sieved or sorted in obtaining fibers within a desired size range.

In some embodiments, the bone particles may have an average diameter, for example, between about 125 microns and about 4 mm; between about 710 microns and about 2 mm; between about 125 microns and about 500 microns; between about 125 microns and about 850 microns; or between about 250 microns and about 710 microns. In some embodiments, the bone particles have a median diameter of about from 10 to 1,000 microns, a median length of about from 0.5 to 100 mm, and a median thickness of about from 10 to 1000 microns. Certain embodiments of the present invention may include bone powder that is commercially available. For example, a suitable bone powder that is widely and reliably available is produced by LifeNet Health, Virginia Beach, Va. (e.g. ground demineralized bone powder, and demineralized bone fiber). In some embodiments, the bone particles may be prepared by grinding, skiving, or Computer Numerical Control (CNC) machining of bone tissues. In some embodiments, the bone particles may be prepared by the methods described in U.S. Pat. No. 7,744,597, which is incorporated by reference herein.

In some embodiments, the bone fibers may have an elongate main body. In the present application, the dimensions of the main body are referred to as the dimensions of the bone fiber. For example, the length of the bone fiber may be between about 100 microns and about 50 mm; between about 200 microns and about 20 mm; between about 500 microns and about 15 mm; between about 600 microns and about 12 mm; between about 700 microns and about 11 mm; between about 700 microns and about 10 mm; between about 700 microns and about 9 mm; between about 700 microns and about 8 mm; between about 700 microns and about 7 mm; between about 700 microns and about 6 mm; between about 900 microns and about 15 mm; between about 900 microns and about 10 mm; or between about 900 microns and about 9 mm. In addition, for example, the width of the bone fibers may be between about 5 microns and about 5 mm; between about 10 microns and about 4 mm; between about 20 microns and about 3 mm; between about 20 microns and about 2 mm; between about 20 microns and about 1.5 mm; between about 20 microns and about 1 mm; between about 20 microns and about 800 microns; between about 20 microns and about 700 microns; between about 20 microns and about 600 microns; between about 70 microns and about 2 mm; between about 70 microns and about 1.5 mm; between about 70 microns and about 1.4 mm; or between about 70 microns and about 1.3 mm.

In some embodiments, the bone fibers in a bone composition may have an average length and an average width. For example, the average length of the bone fibers may be between about 1 mm and about 10 mm; between about 1.5 mm and about 5 mm; between about 2 mm and about 4 mm; between about 2.5 mm and about 3 mm; between about 3 mm and about 5 mm; between about 3 mm and about 4 mm; or between about 3.5 mm and about 4 mm. The average width of the bone fibers may be between about 50 microns and about 1 mm, between about 100 microns and about 800 microns, between about 150 microns and about 700 microns, between about 200 microns and about 500 microns, between about 200 microns and about 400 microns, between about 200 microns and about 300 microns, between about 200 microns and about 250 microns, between about 300 microns and about 500 microns, between about 300 microns and about 400 microns, between about 400 microns and about 500 microns, or between about 400 microns and about 450 microns. The average length of the bone fibers may be less than 20 mm, 10 mm, 9 mm, 8 mm, 7 mm, 6 mm, 5 mm, 4 mm, or 3 mm. The average length of the bone fibers may be more than 500 microns, 1 mm, 1.5 mm, 2 mm, 2.5 mm, 3 mm, 3.5 mm, 4 mm, 4.5 mm, or 5 mm. The average width of the bone fibers may be less than 1 mm, 900 microns, 800 microns, 700 microns, 600 microns, 500 microns, 400 microns, 300 microns, or 250 microns. The average width of the bone fibers may be more than 10 microns, 20 microns, 30 microns, 40 microns, 50 microns, 75 microns, 100 microns, 150 microns, 200 microns, 300 microns, 400 microns, or 500 microns.

Certain embodiments of the present invention may include bone powder that is commercially available. For example, a suitable bone product that is widely and reliably available is produced by LifeNet Health, Inc., Virginia Beach, Va. (e.g. demineralized bone fiber). In some embodiments, the bone particles and/or fibers may be prepared by grinding, skiving, and/or Computer Numerical Control (CNC) machining of bone tissues. In some embodiments, the bone particles and/or fibers may be prepared by the methods described in U.S. Pat. No. 7,744,597, which is incorporated by reference herein.

In some embodiments, the bone fibers may comprise microfibers. The microfibers may comprise projections or spikes extending from the main body of the bone fibers, but have a significantly less width or diameter compared with the main diameter of the bone fibers. A microfiber may have a length, which is the measurement of the tip of the microfiber to where the microfiber connects to the main body of the bone fiber. The average length (L) of the microfibers represents the average of lengths for a representative number of microfibers from a sample. A microfiber may have a width, which is an average measurement of the microfiber's diameter. The average width (W) of the microfibers represents the average of widths for a representative number of microfibers from a sample.

In some embodiments, the width of the microfibers may range from about 0.5 to about 100 microns; in some embodiments, the width of the microfibers may range from about 0.1 to about 30 microns; in some embodiments, the width of the microfibers may range from about 0.2 to about 20 microns; in some embodiments, the width of the microfibers may range from about 0.2 to about 10 microns; in some embodiments, the width of the microfibers may range from about 0.2 to about 3 microns. In some embodiments, the average width (W) of the microfibers may range from about 0.5 to about 20 microns, in some embodiments, the average width (W) of the microfibers may range from about 0.8 to about 10 microns; in some embodiments, the average width (W) of the microfibers may range from about 0.8 to about 6 microns; in some embodiments, the average width (W) of the microfibers may range from about 0.8 to about 3 microns; in some embodiments, the average width (W) of the microfibers may range from about 0.8 to about 2 microns; in some embodiments, the average width (W) of the microfibers may range from about 0.8 to about 1.5 microns; in some embodiments, the average width (W) of the microfibers may range from about 0.8 to about 1.4 microns. In some embodiments, the average width (W) may be less than about 6 microns, 5 microns, 4 microns, 3 microns, 2 microns, 1.6 microns, 1.5 microns, 1.4 microns, 1.3 microns, 1.2 microns, 1.1 microns, 1 micron, or 0.9 micron. In some embodiments, the average width (W) may be more than about 0.2 micron, 0.3 micron, 0.4 micron, 0.5 micron, 0.6 micron, 0.7 micron, 0.8 micron, 0.9 micron, 1 micron, 1.1 microns, 1.2 microns, 1.3 microns, or 1.35 microns.

In some embodiments, the length of the microfibers may range from about 0.5 to about 100 microns; in some embodiments, the length of the microfibers may range from about 1 to about 50 microns; in some embodiments, the length of the microfibers may range from about 2 to about 50 microns; in some embodiments, the length of the microfibers may range from about 3 to about 20 microns; in some embodiments, the length of the microfibers may range from about 3 to about 16 microns; in some embodiments, the length of the microfibers may range from about 3 to about 11 microns. In some embodiments, the average length (L) of the microfibers may range from about 3 to about 20 microns, in some embodiments, the average length (L) of the microfibers may range from about 4 to about 15 microns; in some embodiments, the average length (L) of the microfibers may range from about 5 to about 13 microns; in some embodiments, the average length (L) of the microfibers may range from about 6 to about 10 microns; in some embodiments, the average length (L) of the microfibers may range from about 6 to about 8 microns; in some embodiments, the average length (L) of the microfibers may range from about 6 to about 7 microns. In some embodiments, the average length (L) of the microfibers may be less than about 20 microns, 15 microns, 12 microns, 10 microns, 9 microns, 8 microns, 7 microns, or 6.5 microns. In some embodiments, the average length (L) of the microfibers may be more than about 0.5 micron, 0.6 micron, 0.7 micron, 0.8 micron, 0.9 micron, 1 micron, 2 microns, 3 microns, 4 microns, 5 microns, 6 microns, 7 microns, 8 microns, 9 microns, or 10 microns.

In some embodiments, the average length (L): average width (W) ratio of the microfibers may range from about 0.5 to 50; in some embodiments, the L:W ratio of the microfibers may range from about 0.8 to 20; in some embodiments, the L:W ratio of the microfibers may range from about 1 to 10; in some embodiments, the L:W ratio of the microfibers may range from about 2 to 8; in some embodiments, the L:W ratio of the microfibers may range from about 2 to 6; in some embodiments, the L:W ratio of the microfibers may range from about 2 to 5; in some embodiments, the L:W ratio of the microfibers may range from about 3 to 20; in some embodiments, the L:W ratio of the microfibers may range from about 3 to 10; in some embodiments, the L:W ratio of the microfibers may range from about 3 to 8; in some embodiments, the L:W ratio of the microfibers may range from about 3 to 6; in some embodiments, the L:W ratio of the microfibers may range from about 4 to 20; in some embodiments, the L:W ratio of the microfibers may range from about 4 to 10; in some embodiments, the L:W ratio of the microfibers may range from about 4 to 8; in some embodiments, the L:W ratio of the microfibers may range from about 4 to 6; in some embodiments, the L:W ratio of the microfibers may range from about 5 to 20; in some embodiments, the L:W ratio of the microfibers may range from about 5 to 10; in some embodiments, the L:W ratio of the microfibers may range from about 5 to 8; in some embodiments, the L:W ratio of the microfibers may range from about 6 to 20; in some embodiments, the L:W ratio of the microfibers may range from about 6 to 10; in some embodiments, the L:W ratio of the microfibers may range from about 7 to 20; in some embodiments, the L:W ratio of the microfibers may range from about 7 to 10; in some embodiments, the L:W ratio of the microfibers may range from about 8 to 20; in some embodiments, the L:W ratio of the microfibers may range from about 9 to 20; and in some embodiments, the L:W ratio of the microfibers may range from about 10 to 20.

In some embodiments, the microfibers may have a L:W ratio that is more than about 0.5, 0.8, 1, 1.5, 2.0, 2.1, 2.2, 2.3, 2.4, 2.5, 3.0, 3.5, 4.0, 4.5, 5.0, 5.5, 6.0, 6.5, 7.0, or 7.5. In some embodiments, the microfibers may have a L:W ratio that is less than about 20.0, 15.0, 14.0, 13.0, 12.0, 11.0, 10.0, 9.5, 9.0, 8.5, 8.0, 7.5, 7.0, 6.5, 6.0, 5.5 or 5.0.

In some embodiments, the mode for the pore size of a dry bone composition may range from 5 to 30 microns, from 5 to 20 microns, from 10 to 500 microns, from 10 to 300 microns, from 10 to 100 microns, from 10 to 50 microns, from 10 to 30 microns, from 10 to 25 microns, from 15 to 25 microns, from 15 to 400 microns, from 20 to 300 microns, from 30 to 200 microns, from 30 to 100 microns, from 35 to 100 microns, from 40 to 100 microns, from 40 to 80 microns, from 40 to 70 microns, from 40 to 60 microns, from 50 to 100 microns, from 50 to 80 microns, from 50 to 70 microns, from 50 to 60 microns, or from 54 to 57 microns. The mode for the pore size of a dry bone composition may be more than about 5, 10, 11, 12, 13, 14, 15, 16, 17, 18, 19, 20, 25, 30, 35, 40, 45, 50, 55, 60, 65, 70, 75, 80, 85, 90, 95 or 100 microns. The mode for the pore size of a dry bone composition may be less than about 500, 400, 300, 200, 150, 100, 90, 80, 70, 60, 50, 40, 30, 29, 28, 27, 26, 25, 24, 23, 22, 21, 20, 19 or 18 microns.

In some embodiments, the mean for the pore size of a dry bone composition may range from 0.05 to 25 microns, from 0.05 to 20 microns, from 10 to 500 microns, from 15 to 400 microns, from 20 to 300 microns, from 30 to 200 microns, from 30 to 100 microns, from 35 to 100 microns, from 35 to 80 microns, from 35 to 70 microns, from 35 to 60 microns, from 35 to 50 microns, from 35 to 45 microns, from 40 to 100 microns, from 40 to 90 microns, from 40 to 80 microns, from 40 to 70 microns, from 40 to 60 microns, or from 40 to 50 microns. The mean for the pore size of a dry bone composition may be more than about 5, 10, 15, 20, 25, 30, 35, 40, 45, 50, 55, 60, 65, 70, 75, 80, 85, 90, 95 or 100 microns. The mean for the pore size of a dry bone composition may be less than about 500, 400, 300, 200, 150, 100, 90, 80, 70, 60, 50, 40, or 30 microns.

The equilibrium state of a wet bone composition is reached when the bone composition is immersed in a solution (e.g. a saline solution or blood or cell suspension) and refuses to accept any more of the liquid. The equilibrium model of the bone composition may mimic the state of the bone composition in vivo. In some embodiments, when the bone composition is immersed in a solution, liquid or fluid, the bone composition swells, resulting in a hydrogel or a moldable putty. In additional embodiments, the bone composition reaches the equilibrium when it is immersed in a solution at least for 5 minutes, 15 minutes, 20 minutes, 30 minutes, 40 minutes, or 50 minutes.

In some embodiments, the mode for the pore size of a wet bone composition at equilibrium may range from 10 to 500 microns, from 15 to 400 microns, from 20 to 300 microns, from 20 to 250 microns, from 20 to 210 microns, from 25 to 250 microns, from 25 to 225 microns, from 25 to 210 microns, from 25 to 200 microns, from 25 to 190 microns, from 25 to 180 microns, from 25 to 170 microns, from 25 to 160 microns, from 25 to 100 microns, from 25 to 50 microns, from 25 to 45 microns, from 25 to 40 microns, from 25 to 35 microns, from 50 to 500 microns, from 50 to 250 microns, from 50 to 200 microns, from 50 to 150 microns, from 50 to 130 microns, from 50 to 120 microns, from 50 to 115 microns, from 50 to 110 microns, from 50 to 1005 microns, from 250 to 500 microns, from 250 to 400 microns, from 250 to 350 microns, from 250 to 300 microns, from 150 to 500 microns, from 150 to 400 microns, from 150 to 350 microns, from 150 to 300 microns, from 150 to 250 microns, from 150 to 240 microns, from 150 to 230 microns, from 150 to 220 microns, or from 150 to 210 microns. The mode for the pore size of a wet bone composition at equilibrium may be more than 5, 10, 15, 20, 30, 40, 45, 46, 47, 48, 49, 50, 51, 52, 53, 54, 55, 60, 70, 80, 90, 100, 110, 120, 130, 140, 150, 160, 170, 180, 190 or 200 microns. The mode for the pore size of a wet bone composition at equilibrium may be less than 500, 400, 300, 250, 240, 230, 220, 210, 200, 190, 180, 170, 160, 150, 140, 130, 120, 110, 109, 108, 107, 106, 105, 104, 100, 90, 80, 70, 60, 50, 45, 40, 35, 30, 25, or 20 microns.

In some embodiments, the mean for the pore size of a wet bone composition at equilibrium may range from 0.1 to 10 microns, 0.1 to 5 microns, 0.1 to 3 microns, from 10 to 300 microns, from 15 to 200 microns, from 20 to 100 microns, from 20 to 90 microns, from 20 to 80 microns, from 20 to 75 microns, from 20 to 70 microns, from 25 to 100 microns, from 25 to 90 microns, from 25 to 80 microns, from 25 to 75 microns, from 25 to 70 microns, from 25 to 65 microns, from 25 to 60 microns, from 25 to 55 microns, from 25 to 51 microns, from 25 to 50 microns, from 50 to 100 microns, from 50 to 90 microns, from 50 to 80 microns, from 50 to 75 microns, or from 50 to 70 microns. The mean for the pore size at equilibrium may be more than 0.1, 0.2, 0.3, 0.4, 0.5, 0.7, 1, 5, 10, 15, 20, 25, 30, 35, 40, 45, 50, 55, 60, 65, 70, 75, 80, 85, 90, 95, 100, 110, 120, 130, 140, or 150 microns. The mean for the pore size at equilibrium may be less than 200, 190, 180, 170, 160, 150, 140, 130, 120, 110, 100, 95, 90, 85, 80, 75, 70, 65, 60, 55, 50, 45, 40, 35, 30, 25, 20, 15, 10, 5, 4, 3, 2, 1, or 0.1 microns.

In some embodiments, the pore size of a wet bone composition at equilibrium has a unimodal distribution. In some embodiments, the pore size of a wet bone composition at equilibrium does not have a notable bimodal distribution. A bimodal distribution may be defined as a pore size distribution having two distinct peaks. A notable bimodal distribution may be defined as a bimodal distribution with a bimodal ratio (the ratio of one peaks versus the other peak) within the range of 0.99 to 1.01, 0.95 to 1.05, 0.9 to 1.1, 0.85 to 1.18, 0.8 to 1.25, 0.7 to 1.43, 0.6 to 1.67, 0.5 to 2, 0.4 to 2.5, 0.3 to 3.33, 0.2 to 5, 0.15 to 6.67, 0.05 to 20, 0.04 to 25, 0.03 to 33, 0.02 to 50, 0.01 to 100, or 0.005 to 200.

As used herein, the term "about" modifying, for example, length, width, distance, the quantity of an ingredient in a composition, concentrations, volumes, process temperature, process time, yields, flow rates, pressures, and like values, and ranges thereof, refers to variation in the numerical quantity that can occur, for example, through typical measuring and handling procedures used for making compounds, compositions, concentrates or use formulations; through inadvertent variation in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. The term "about" further may refer to a range of values that are similar to the stated reference value. In certain embodiments, the term "about" refers to a range of values that fall within 20, 19, 18, 17, 16, 15, 14, 13, 12, 11, 10, 9, 8, 7, 6, 5, 4, 3, 2, 1 percent or less of the stated reference value.

In one aspect, the compressed bone compositions do not comprise a binder or a chemical cross-linker. In another aspect, a binder and/or a chemical cross-linker may be included in the compressed bone compositions. In some embodiments, such binders include, but are not limited to, glycerol/Preservon®, acidic solutions (e.g. Lactic and trifluoroacitic acid), buffering solutions (e.g. phosphate), and adhesive binders (e.g. fibrin glues, bone cements, or liquified bone). In another aspect, crosslinking may be performed for the bone particles and/or fibers before or after applying the pressure by any conventional chemical crosslinking method (e.g. chemical reagent-promoted, chemically reactive linker-promoted and/or enzyme-promoted) and/or dehydrothermal crosslinking method (e.g. heat-promoted condensation), forming a covalently crosslinked bone matrix. In additional embodiments, the crosslinking comprises applying a cross-linking agent to the bone matrix solution. For example, the cross-linking agent may be selected from the group consisting of 1-Ethyl-3-(3-dimethylaminopropyl)carbodiimide (EDC), EDC/hyaluronic acid, genipin, and glutaraldehyde.

The bone from which the bone particles and/or fibers are derived includes, but is not limited to, autograft bone, allograft bone, and xenograft bone. Such bone includes any bone from any source, including, but not limited to, bone from a living human donor, bone from a human cadaveric donor, and bone from a living or non-living animal. The bone from which the fibers are derived may include cortical bone and/or cancellous bone and/or cortico-cancellous bone. The bone from which the fibers are derived may be obtained from any mammal, including but not limited to a human, a cow, a pig, a dog, a cat, a non-human primate, a rodent such as a rat or mouse, a horse, a goat, a sheep, or a deer.

The bone from which the bone particles and/or fibers are derived may be demineralized bone, partially demineralized bone or non-demineralized bone. In one aspect, the bone particles and/or fibers may be demineralized prior to applying the pressure according to the methods of the present invention. "Demineralized bone" as used herein refers to bone having less than about 8 wt % residual calcium. In some embodiments, the demineralized bone has an average residual calcium content of less than 7, 6, 5, 4, 3, 2 or 1 wt %. In some embodiments, the demineralized bone has an average residual calcium content of from 0 to 4, from 0.5 to 4, from 1 to 4, from 2 to 4, from 3 to 4, from 0 to 3, from 0.5 to 3, from 1 to 3, from 2 to 3, from 0 to 2, from 1 to 2, or from 0 to 1 wt %. Demineralization involves treating a bone tissue to remove its inorganic mineral hydroxyapatite material. The level of demineralization of a bone tissue is defined by the amount (wt %) of residual calcium found in the demineralized bone. In some embodiments, the demineralized bone may still contain physiologically active levels of growth and differentiation factors (e.g., osteogenic growth factors, such as bone morphogenetic proteins (BMPs) and insulin like growth factor (IGF)) remaining from the initial bone even after the demineralization treatment. In further embodiments, the demineralized bone may contain collagen, osteocalcin, osteonectin, bone sialo protein, osteopontin, and mixtures thereof. In one embodiment, the bone particles and/or fibers are prepared from demineralized bone. In other embodiment, the bone particles and/or fibers are prepared from non-demineralized bone tissue and the fibers are demineralized after bone fiber formation. "Non-demineralized bone" as used in the present application refers to bone that has not been treated to remove minerals present such as, for example, hydroxyapatite.

The bone particles and/or fibers of the present invention may be demineralized or non-demineralized. In some embodiments, the bone particles and/or fibers may be combined with other bone materials, such as bone powders and/or bone particulates, which may be demineralized or non-demineralized or synthetic. In some embodiments, the bone compositions and/or bone implants of the present invention may comprise bone particles and/or fibers and/or other bone materials, such as bone powders and bone particulates, which may be demineralized or non-demineralized or synthetic. In additional embodiments, the bone implant may be combined with prosthesis with or without adhesion.

In some embodiments, the bone particles and/or fibers, bone compositions, and/or bone implants may be cleaned after or before applying the pressure. In some embodiments, the cleaning comprising incubating the bone particles and/or fibers with an antibiotic, a detergent, an alcohol, and/or a $H_2O_2$. In some embodiments, the cleaning comprises ALLOWASH® process. In some embodiments, the cleaning includes methods described in U.S. Pat. Nos. 5,556,379, 5,797,871, 5,820,581, 5,977,034, and 5,977,432, each of which is incorporated by reference herein. In additional embodiments, the cleaning excludes use of alcohol.

In one aspect, the bone particles and/or fibers, bone compositions, and/or bone implants may be sterilized after or before applying the pressure. In some embodiments, the bone particles and/or fibers, compressed bone compositions, and/or bone implants may be sterilized by gamma or e-beam irradiation, ethylene oxide, or critical $CO_2$.

In one aspect, the bone particles and/or fibers, bone compositions, and/or bone implants may be treated with a plasticizer composition. In some embodiments, the plasticizer composition comprises one or more plasticizers selected from the group consisting of glycerol, adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline, polyol, and a fatty acid. For example, the plasticizer composition may include those described in U.S. Pat. Nos. 6,293,970 and 7,063,726, and U.S. Patent Application Publication Nos. 2010/0030340 and 2010/0185284, each of which is incorporated by reference herein.

In some embodiments, the bone particles and/or fibers, bone compositions, and/or bone implants may be cleaned before or after being sterilized, before or after applying the pressure, and before or after being treated with a plasticizer composition. In some embodiments, the bone particles and/or fibers, bone compositions, and/or bone implants may be sterilized before or after being cleaned, before or after applying the pressure, and before or after being treated with a plasticizer composition. In some embodiments, the bone particles and/or fibers, bone compositions, and/or bone implants may be compressed before or after being cleaned, before or after being sterilized, and before or after being treated with a plasticizer composition. In some embodiments, the bone particles and/or fibers, bone compositions, and/or bone implants may be treated with a plasticizer composition before or after being cleaned, before or after being sterilized, and before or after applying the pressure.

The invention relates to methods of preparing compressed bone compositions comprising loading bone particles and/or fibers into a mold with a predetermined shape, applying pressure to the bone particles and/or fibers, and freeze drying the compressed bone particles and/or fibers.

In some embodiments, the pressure applied to the bone particles and/or fibers may range from about 1 Pa to about 300 MPa; in some embodiments, the pressure applied to the bone particles and/or fibers may range from about 100 Pa to about 100 MPa, from about 1 KPa to about 100 MPa, from about 10 KPa to about 100 MPa, from about 100 KPa to about 100 MPa, from about 1 MPa to about 100 MPa, from about 100 KPa to about 1 MPa, from about 100 KPa to about 2 MPa, from about 100 KPa to about 3 MPa, 100 KPa to about 4 MPa, 100 KPa to about 5 MPa, 100 KPa to about 6 MPa, about 1 MPa to about 2 MPa, from about 1 MPa to about 3 MPa, from about 1 MPa to about 4 MPa, from about 1 MPa to about 5 MPa, from about 1 MPa to about 6 MPa, from about 1 MPa to about 7 MPa, from about 2 MPa to about 3 MPa, or from about 2 MPa to about 6 MPa; and in some embodiments, the pressure applied to the bone particles and/or fibers may range between 100 psi and 5000 psi, between 100 psi and 4000 psi, between 100 psi and 3000 psi, between 100 psi and 2000 psi, between 100 psi and 1000 psi, between 100 psi and 990 psi, between 100 psi and 950 psi, between 100 psi and 905 psi, between 200 psi and 5000 psi, between 200 psi and 4000 psi, between 200 psi and 3000 psi, between 200 psi and 2000 psi, between 200 psi and 1000 psi, between 200 psi and 990 psi, between 200 psi and 950 psi, or between 200 psi and 905 psi (not including the end values).

In some embodiments, the pressure applied to the bone particles and/or fibers may be about 1, 2, 3, 4, 5, 6, 6.5, 7, 8, 9, 10, 11, 12, 13, 14, 15, 20, 21, 22, 23, 24, 25, 26, 27, 28, 29, 30 or 40 MPa or less. In other embodiments, the pressure applied to the bone particles and/or fibers may be about 0.1, 0.5, 1, 2, 3, 4, 5, 6, 6.5, 7, 8, 9, 10, 11, 12, 13, 14, 15, 20, 21, 22, 23, 24, 25, 26, 27, 28, 29, 30 or 35 MPa or more. In some embodiments, the pressure applied to the bone particles and/or fibers may be about 6000, 5000, 4000, 3000, 2000, 1000, 900, 800, 700, 600, 500, 400, 300, or 200 psi or less. In other embodiments, the pressure applied to the bone particles and/or fibers may be about 100, 200, 300, 400, 500, 600, 700, 800, or 900 psi or more. In one aspect, the pressure may be applied using a screw type press or a pneumatic press to generate the requisite pressure. In another aspect, the pressure may be applied using a hydraulic press, application of a heavy weight, or a spring loaded device, powder-actuated, clamped, or electric motor-based pressurizations, either as constant pressure or variable pressure device. In another aspect, the pressure may be applied for at least about 1, 2, 3, 4, 5, 10, 15, 20, 30, 40, 50, 60, 120, 180, 240, 300, or 360 minutes.

The pressure may be applied with any kind of mechanical force and with or without any device. In some embodiments, the pressure may be applied by a human, e.g. pressing with hands and/or fingers. In some embodiments, the pressure may be applied by a device customized to produce compressed bone compositions.

In some embodiments, the invention also related to a method for preparing an individualized bone implant, comprising: loading bone composition into a mold that is based upon three dimensional (3D) measurements taken from a bone structure of the individual for the implant or prosthesis, wherein the bone composition comprises microfibers having an average length (L): average width (W) ratio greater than about 2; applying pressure of from 0.1 to 30 MPa to the bone composition to fit the mold; and freeze drying the compressed bone composition to make the bone implant. In additional embodiments, the method may include adding prosthesis to bone implant with or without adhesion. The prosthesis is a synthetic implant comprising a material(s) that does not occur naturally in bone. The prosthesis may include, for example, a metal(s) and a polymer(s), such as titanium, gold, platinum and steel with or without teflon.

The predetermined shape of the mold and the resulting compressed bone compositions include various sizes and structures, which may be reflected by the 3D measurements of a bone structure of a subject. The 3D measurements are a set of dimensions and values that represent the size and shape of the bone structure and the possibly relative positioning and interactions of the various components of the bone structure, or between the patient bone structure and any concurrently implanted prosthetic devices to which the custom cast fibers are also designed to fit and integrate with. The predetermined shape of the mold may be constructed by 3D printing of the mold based on the 3D medical imaging measurements. The custom shaped molds may also be constructed by CNC and other common modes of machining by subtractive manufacturing. Any suitable 3D printing technology and device or any additive manufacturing technology and apparatus may be used for the current method.

The bone structure herein described may be any bone structure, including one or more components, from any part of the skeleton of a human or an animal. For example, the bone structure may be any segmental defect without load bearing. In some embodiments, the bone structure may be a vertebrate or a portion thereof, a femoral head or a femur trochanter, a humeral head from a humerus, or a segment or part of the fibula, humeral shaft, femoral shaft, pelvis, cranial bones, facial bones, hip, skull flap, mandible or tibia.

An "implant" refers to any object that is designed to be placed partially or wholly within a subject's body for one or more therapeutic or prophylactic purposes such as for tissue augmentation, contouring, restoring physiological function, repairing or restoring tissues damaged by disease or trauma, and/or delivering therapeutic agents to normal, damaged or diseased organs and tissues. In one aspect, the bone implant comprises grooves as described herein. The subject may be any human or non-human mammal, such as dog, horse, or primate in need of a bone implant. An "individualized implant" refers to an implant that is specifically designed and produced based on the 3D measurements of an individual subject or the average of a number of individual subjects. The individualized implant may provide a better structural fit for the subject's bones that are to be repaired or restored.

In one aspect, the predetermined shape of the mold and the resulting compressed bone compositions comprise grooves and/or undulations, where the compositions or implants are thinner in some portions than in other portions of the compositions or implants, respectively. The "groove" is an area that is designed to have a thickness that is thinner than the thickness of the surrounding areas permitting a point, line, or area of bending, pivoting, and/or shaping. In one embodiment, this variation in thickness of the compositions and implants allows the compositions and implants to be more flexible than compositions and implants of uniform thickness, such that the compositions and implants may be bent, pivoted, shaped or twisted. In select embodiments, the grooves or undulations in the compressed bone compositions and/or the bone implants may have a periodicity at least of 0.5, 2, 5 or 10 grooves/cm$^2$. In additional embodiments, the groove(s) in the compressed bone compositions and/or the bone implants may have a periodicity at most of 2, 5, 10 or 15 grooves/cm$^2$. In additional embodiments, the predetermined shape of the compressed bone compositions may include pre-existing holes to allow for fixation with screws, sutures, or other types of traction. Such holes may be formed as a part of the mold and/or fiber product design.

In one aspect of the present invention, the compositions and implants maintain their integrity in liquids for at least about 5, 15, 30, 100, or 200 minutes. Thus, the compressed bone compositions described herein may retain the structural integrity prior to and during surgical implantation after rehydration. As used herein, the phrase "maintain integrity" when used in conjunction with the compositions and implants of the present invention is used to indicate that all of part of the fibers of the compositions and implants do not dissociate from one another, and the compositions and implants maintain their overall shape in the presence of liquids, such as buffers and body fluids. For example, at least 50, 60, 70, 80, 85, 90, 95, or 98 wt % of the original fibers of the compositions remain in the implant after 0.1, 1, 10, 100, 150, 200, or 300 hours.

In some embodiments, various methods may be applied to alter the wettability of bone particles and/or fibers and resulting compressed bone fiber strip described herein. Some examples include both physical and chemical means, including surface chemistry modifications (e.g. with plasma or changing the static charge, or by making large passages or channels for water to enter), chemical etching (e.g. acid etching), and addition of a hydrophilic molecule (e.g. Preservon).

In some embodiments, the average thickness of the predetermined shape of the mold or the resulting compressed bone composition at the groove(s) may be thinner than the average thickness of the entire predetermined shape or the compressed bone composition, for example, by about 1%, 2%, 3%, 5%, 10%, 20%, 30%, 40%, 50%, 60%, 70%, 80%, or 90%. In some embodiments of the present disclosure, the compressed bone composition has a higher density at the groove area(s) compared to rest of the structure, for example, by about 1%, 2%, 3%, 5%, 10%, 20%, 30%, 40%, 50%, 60%, 70%, 80%, or 90%.

In another aspect, the predetermined shape of the mold and the resulting compressed bone compositions have shapes that include a strip, a disc, with a concave facet, with a convex facet, with either flat features, with steps, or with curves, comprising, but not limited to, waves, with bubbles, or with a bubble-wrap patterns. In some embodiments, other shapes may be used, including, but not limited to, cylinder, tubes (e.g. for filling with BMA, autograft, PRP, and other bioactive agents), thin sheets for rolling in autograft or wrapping around defects, mating with synthetic implants (e.g. plugs for intervertebral fusion device cavities, hollow part for fitting onto screws or other devices, such as a spinous process fusion plate, etc.), ring type designs (e.g. for segmental defects), acetabular cup, ball or sphere shaped (e.g. ball and socket revisions and resurfacing, and ball shaped implants in the thoracic spine and other areas) oral/cranial/maxillofacial applications such as strips or alveolar ridge reconstruction, and wedges (e.g. for Evans, Cotton, high tibial osteotomy), and irregular shapes and custom shapes that are patient defect specific, potentially as based on computed tomography (CT) or X-ray scans. The compressed bone particles and/or fibers may be used to fill a load bearing material (e.g. mineralized cortical or conricocancellous bone, metal, PEEK, synthetic polymers, and cages) to supply a source of osteoinductive and/or osteoconductive fibers in a non-inductive graft. For example, the shapes may include a conical or frustum shaped dowel to fill a hole such as a surgical screw hole. The compressed bone particles and/or fibers may also be non-load bearing.

In one aspect of the present invention, the compressed bone composition may be used to prepare a combination product with a synthetic or metallic structure, e.g. a framework, where the compressed bone composition and the synthetic or metallic structure are tethered or bound together. In some embodiments, the synthetic or metallic structure may facilitate surgical fixation or stabilization of the combination product to the defect site, while the new tissue can form on and within the compressed bone composition, and remodel the composition partially or completely. The surgeon may then remove the synthetic or metallic structure. A traditional composition cannot be used in this approach since it is likely to dissemble during the healing and tissue forming processes.

In another aspect, the predetermined shape of the mold and the resulting compressed bone compositions have at least one dimension of about 0.5 mm, 1 mm, 5 mm, 10 mm, 20 mm, 30 mm, 40 mm, 50 mm, 60 mm, 70 mm, 80 mm, 90 mm, 100 mm, 200 mm, 300 mm. In another aspect, the predetermined shape of the mold and the resulting compressed bone compositions have variable sizes from about 1×1×1 mm to about 100×100×10 mm, or about 100 mm×25 mm with 1 to 8 mm thickness.

In one aspect, the bone particles and/or fibers may be directly compressed, with or without an additional mold, into or onto a load bearing material (e.g. mineralized cortical bone, including, but not limited to, femur sectioned as a hollow disc) or other hard materials (e.g. ceramics, metals).

The bone particles and/or fibers may be freeze-dried to produce the compressed bone compositions. In additional embodiments, the compressed bone particles and/or fibers may be vacuum dried, heated (e.g. at a temperature from 37 to 41° C.), and/or dehydrothermal treated. In some embodiments, the bone particles and/or fibers, bone compositions, and/or bone implants may be freeze-dried before or after applying the pressure.

In one aspect, the pressure is applied to the bone particles and/or fibers at room temperature, which is defined as about 25° C. In another aspect, the pressure is applied to the bone particles and/or fibers at other temperatures, including, but not limited to, at least about 100° C., 90° C., 80° C., 70° C., 60° C., 50° C., 45° C., 40° C., 35° C., 34° C., 33° C., 32° C., 31° C., 30° C., 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., 10° C., 5° C. or higher. In another aspect, the pressure is applied to the bone particles and/or fibers at other temperatures, including, but not limited to, less than about 100° C., 90° C., 80° C., 70° C., 60° C., 50° C., 45° C., 40° C., 35° C., 34° C., 33° C., 32° C., 31° C., 30° C., 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., 10° C., or 5° C.

The invention also relates to bone implants prepared by the methods of the present invention. In one aspect, the bone implant may not be a load bearing implant. The bone implant describe herein may have a wet compressive strength of less than 3 MPa, 2 MPa, 1 MPa, 0.5 MPa, or 0.1 MPa.

In one aspect, the bone compositions comprising the bone implant and/or bone implants further comprise at least one cell and/or at least one bioactive factor. The term "bioactive factor" refers to a protein, carbohydrate, or mineral that has any effect on a cellular activity. Examples of bioactive factors include, but are not limited to, an osteogenic growth factor, collagen, glycosaminoglycans, osteonectin, bone sialo protein, an osteoinductive factor, a chondrogenic factor, a cytokine, a mitogenic factor, a chemotactic factor, a transforming growth factor (TGF), a fibroblast growth factor (FGF), an angiogenic factor, an insulin-like growth factor (IGF), a platelet-derived growth factor (PDGF), an epidermal growth factor (EGF), a vascular endothelial growth factor (VEGF), a nerve growth factor (NGF), a neurotrophin, a bone morphogenetic protein (BMP), osteogenin, osteopontin, osteocalcin, cementum attachment protein, erythropoietin, thrombopoietin, tumor necrosis factor (TNF), an interferon, a colony stimulating factor (CSF), or an interleukin, among others. The bioactive factor may be a BMP, PDGF, FGF, VEGF, TGF, insulin, among others. Examples of BMPs include but are not limited to BMP-2, BMP-3, BMP-4, BMP-5, BMP-6, BMP-7, BMP-8, BMP-9, BMP-10, BMP-11, BMP-12, BMP-13, BMP-14, BMP-15, any truncated or modified forms of BMP-2, BMP-3, BMP-4, BMP-5, BMP-6, BMP-7, BMP-8, BMP-9, BMP-10, BMP-11, BMP-12, BMP-13, BMP-14, or BMP-15, and a mixture thereof.

In some embodiments, the bioactive factor may include chemokines. Chemokines refers to a family of small proteins secreted from cells that promote the movement or chemotaxis of nearby cells. Some chemokines are considered pro-inflammatory and may be induced during an immune response while others are considered homeostatic. Typically, chemokines exert their chemoattractant function and other functions by binding to one or more chemokine receptors. Chemokines include proteins isolated from natural sources as well as those made synthetically, by recombinant means or by chemical synthesis. Exemplary chemokines include, but are not limited to, MCP-1, Eotaxin, SDF-1β, GRO-α, MIP-1β, IL-8, IP-10, MCP-3, MIP-3α, MDC, MIP-1α, BCA-1, GCP-2, ENA-78, PBP, MIG, PF-4, PF-4-var1, SDF-2, MCP-2, MCP-4, MIP-4, MIP-3β, MIP-2α, MIP-2β, MIP-5, HCC-1, RANTES, Eotaxin-2, TARC, I-309, Lymphotactin, Lungkine, C10, MIP-1γ, MCP-5, LEC, Exodus-2, MIP-3, TECK, Eotaxin-3, CTACK, MEC, SCM-1β, I-TAC, BRAK, SR-PSOX, Fractalkine, LD78-β, MIP-1b2, and others known to those of skill in the art. References to chemokines typically include monomeric forms of such chemokines. Chemokines also include dimeric or other multimeric forms.

In additional embodiments, the bioactive factor may also include small molecules. Small molecules include molecules, whether naturally-occurring or artificially created (e.g., via chemical synthesis) that has a relatively low molecular weight and that is not a protein, a nucleic acid, or a carbohydrate. In one aspect, the small molecule is one that has already been deemed safe and effective for use by the appropriate governmental agency or body. For example, drugs for human use listed by the FDA under 21 C.F.R. §§ 330.5, 331 through 361 and 440 through 460; drugs for veterinary use listed by the FDA under 21 C.F.R. §§ 500 through 589, incorporated herein by reference, are all considered acceptable for use as the small molecules in the present disclosure. In another aspect, the small molecules may include agonists of a Sphingosine-1-phosphate (S1P)

agonist, such as fingolimod (FTY720), which is a synthetic compound that acts as an agonist of the S1P1, S1P3, S1P4, and SIP5 receptors when phosphorylated into FTY720P. For example, the small molecule drugs may include the following molecules:

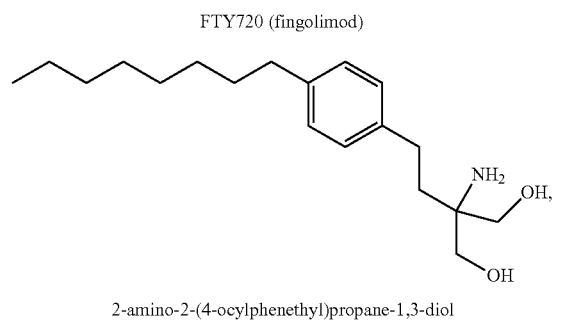

FTY720 (fingolimod)

2-amino-2-(4-ocylphenethyl)propane-1,3-diol

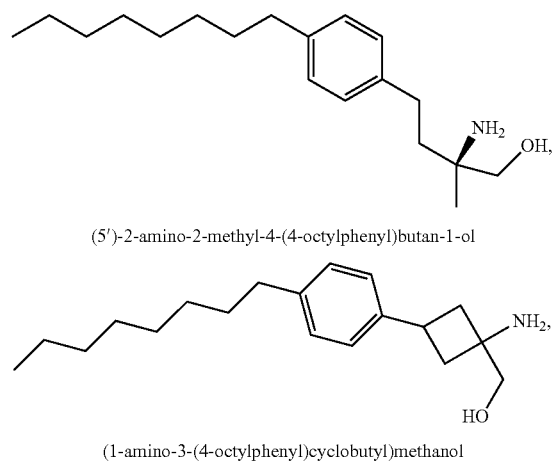

(5′)-2-amino-2-methyl-4-(4-octylphenyl)butan-1-ol (1-amino-3-(4-octylphenyl)cyclobutyl)methanol (1-amino-3-(4-octylphenyl)cyclopentyl)methanol

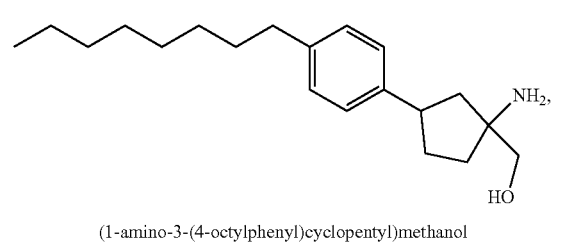

(1-amino-2-(4-octylbenzyl)cyclopentyl)methanol

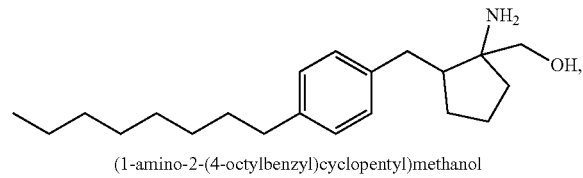

2-amino-2-(6-octyl-1,2,3,4-tetrahydronaphthalen-2-yl)propane-1,3-diol

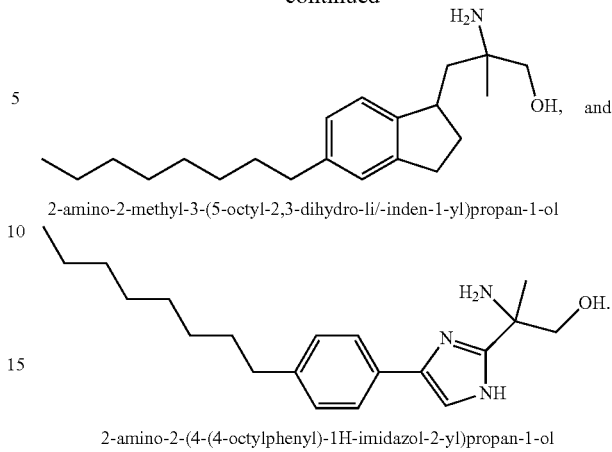

2-amino-2-methyl-3-(5-octyl-2,3-dihydro-li/-inden-1-yl)propan-1-ol 2-amino-2-(4-(4-octylphenyl)-1H-imidazol-2-yl)propan-1-ol In one aspect, the bone compositions and/or bone implants further comprise an accessory polymer. An "accessory polymer" refers to a polymer that may be added to the compressed bone compositions and/or bone implants described herein and have any effect on their physical, chemical, and/or biological properties (e.g. tensile strength, hydrophillicity, biocompatibility). For example, the accessory polymer may be selected from the group consisting of polycaprolactone, poly(glycolic acid), poly(lactic acid), polydioxanone, poly (lactide-co-glycolide) copolymers, polyesters polysaccharides, polyhydroxyalkanoates, starch, polylactic acid, cellulose, proteins, agar, silks, alginate, collagen/gelatin, carrageenan, elastin, pectin, resilin, konjac, adhesives, gums, polyamino acids, polysaccharides, soy, zein, wheat gluten, casein, chitin/chitosan, serum albumin, hyaluronic acid, lipids/s urfactants, xanthan, acetoglycerides, waxes, surfactants, dextran, emulsan, gelian, polyphenols, levan, lignin, curd, ian, tannin, polygalactosamine, humic acid, shellac, pullulan, poly-gamma-glutamic acid, elsinan, natural rubber, yeast glucans, and synthetic polymers from natural fats and oils.

In another aspect, the bone compositions and/or bone implants further comprise one or more biocompatible fillers. The biocompatible fillers may include, but are not limited to, tricalcium phosphate, hydroxyl apatite, and other bioceramics, and bone pieces of various sizes (e.g. as particulate or other sized fibers or other geometries, and either cortical and/or cancellous) mixed into the shaped DBM fibers. The biocompatible fillers may serve as osteoinductive or osteoconductive matrices. For example, these fillers may be added to the CNC fibers during pressing to result in a strip (or other shape) with the mixed materials.

In another aspect, the bone compositions and/or bone implants further comprise one or more biodegradable, biocompatible polymers. The biodegradable, biocompatible polymers may include, but are not limited to, ethylene vinyl acetate, polyanhydricles, polyglycolic acid, collagen, polyorthoesters, and polylactic acid. The biodegradable, biocompatible polymers may further include a number of synthetic biodegradable polymers that may serve as osteoconductive or chondroconductive biocompatible matrices with sustained release characteristics. Descriptions of these polymers can be found in Behravesh (1999) Clinical Orthopaedics 367, S118 and Lu (2000) Polymeric Delivery Vehicles for Bone Growth Factors in Controlled Drug Delivery: Designing Technologies for the Future, Park and Mrsny eds., American Chemical Society, which is incorporated herein in its entirety. Examples of these polymers include polyα-hydroxy esters such as polylactic acid/polyglycolic acid homopolymers and copolymers, polyphosphazenes (PPHOS), polyanhydrides and poly(propylene fumarates).

Polylactic acid/polyglycolic acid (PLGA) homo and copolymers are well known in the art as sustained release vehicles. The rate of release of the bioactive factors described herein may be adjusted by the skilled artisan by variation of polylactic acid to polyglycolic acid ratio and the molecular weight of the polymer (see Anderson (1997) Adv. Drug Deliv. Rev. 28:5. The incorporation of PEG into the polymer as a blend to form microparticle matrices allows further alteration of the release profile of the active ingredient (see Cleek (1997) J. Control Release 48, 259). Ceramics such as calcium phosphate and hydroxyapatite may also be incorporated into the sustained release vehicles to improve mechanical qualities.

In another aspect, the bone compositions and/or bone implants further comprise an extracellular matrix component. For example, the extracellular matrix component may include, but is not limited to, collagen, glycosaminoglycans, osteocalcin, osteonectin, bone sialo protein, osteopontin, or mixtures thereof.

In one aspect, the density of the bone implants and/or bone compositions is about 0.23, 0.24, 0.25, 0.26, 0.28, 0.30, 0.32, 0.33, 0.34, 0.35, 0.40, 0.50, 0.60 or 0.70 g/cm$^3$ or smaller. In another aspect, the density of the bone implants and/or bone compositions is about 0.22, 0.23, 0.24, 0.26, 0.28, 0.30, 0.32, 0.33, 0.34, or 0.35 g/cm$^3$ or more. In another aspect, the density of the bone implants and/or bone compositions is from about 0.1 to about 0.7, from about 0.1 to about 0.6, from about 0.2 to about 0.7, from about 0.2 to about 0.6, from about 0.2 to about 0.5, from about 0.2 to about 0.4, from about 0.2 to about 0.3 g/cm$^3$.

The invention also relates to methods of promoting osteoinductivity, with the methods comprising culturing cells on a bone composition described herein. The invention further relates to methods of promoting osteoconductivity, with the methods comprising culturing cells on a bone composition described herein. As used herein, "osteoinductivity" may refer to causing cells to differentiate into cells that are more osteoblast-like (e.g. in phenotype or in gene and protein expressions), or the term may refer to increasing the proliferation of osteoblasts, or both. "Osteoconductivity" may refer to accelerating the deposition of new bone or the rate of bone growth. The cells, prior to culture on the bone composition and/or bone implant of the present invention, may be undifferentiated or partially differentiated cells. The cells may be present in culture or in a tissue, organ or portion thereof or in an organism. The osteoinductive and/or osteoconductive activity of the bone composition may or may not be altered, including but not limited to, enhanced activity, relative to other compositions without the properties, e.g. the dimensions and L:W rations of the microfibers, described herein.

The invention also relates to methods of promoting chondroinductivity, with the methods comprising culturing cells on a bone composition described herein. The invention further relates to methods of promoting chondroconductivity, with the methods comprising culturing cells on a bone composition described herein. As used herein, "chondroinductivity" may refer to causing cells to differentiate into cells that are more chondrocyte-like (e.g. in phenotype or in gene and protein expressions), or the term may refer to increasing the proliferation of chondrocytes, or both. "Chondroconductivity" may refer to accelerating the deposition of new cartilage or the rate of cartilage growth. The cells, prior to culture on the bone composition of the present invention, may be undifferentiated or partially differentiated cells. The cells may be present in culture or in a tissue, organ or portion thereof or in an organism. The chondroinductive and/or chondroconductive activity of the bone composition may or may not be altered, including but not limited to, enhanced activity, relative to other compositions without the properties, e.g. the dimensions and L:W ratios of the microfibers, described herein.

Thus, the osteoconductive or chondroconductive activity of the bone composition of the present invention may be enhanced compared to other bone compositions. Of course, the bone compositions are considered to be osteoconductive or chondroconductive if cells within the biocompatible matrix begin to differentiate into more osteoblast-like or chondrocyte-like appearing or functional cells, respectively.

The invention also relates to methods of promoting ligament/tendon differentiation and/or growth, with the methods comprising culturing cells on a bone composition described herein. As used herein, "ligament/tendon differentiation" may refer to causing cells to differentiate into cells that are more ligament and/or tendon-like (e.g. in phenotype or in gene and protein expressions), or the term may refer to increasing the proliferation of ligament and/or tendon, or both. "ligament/tendon differentiation growth" may refer to accelerating the deposition of new ligament/tendon or the rate of ligament/tendon growth. The cells, prior to culture on the bone composition of the present invention, may be undifferentiated or partially differentiated cells. The cells may be present in culture or in a tissue, organ or portion thereof or in an organism. The ligament/tendon differentiation activity of the bone composition may or may not be altered, including but not limited to, enhanced activity, relative to other compositions without the properties, e.g. the dimensions and L:W rations of the microfibers, described herein.

There are a variety of osteoblast, chondrocyte, ligament/tendon differentiation markers that may be measured to assess osteoinductivity, chondroinductivity, or ligament/tendon differentiation, respectively. For example, cells express alkaline phosphatases during the early stages of differentiation toward osteoblast lineages. Therefore, in vitro alkaline phosphatase assays may be used to evaluate osteoinductivity in cells cultured on the bone composition described herein. The ability of the bone composition of the present invention to stimulate or induce the alkaline phosphatase expression in an otherwise non-bone forming cells, such as myoblast (C2C12 cells), would indicate that the bone composition of the present invention has osteoinductive activity. In these assays, cells cultured on other bone composition without the properties described herein are used as negative controls to show that the baseline alkaline phosphatase expression on non-bone forming cells. The baseline of the osteoblastic markers in the negative control need not be zero, meaning that the cells in the negative control group may have at least some level of phenotypic marker(s). Accordingly, an "osteoinductive" bone composition of the present invention would simply cause an increase in the osteoblastic markers in experimental cells over control grown on the other compositions. Similarly, chondrocyte markers, including but not limited to type X collagen, type II collagen, Sox 9, Aggrecan. Matrilin-1 and CEP-68, to name a few, may be used to assess chondroinductive potential. Moreover, ligament/tendon markers, including but not limited to scleraxis, may be used to assess ligament/tendon differentiation potential.

Moreover, osteoinductivity, chondroinductivity, and ligament/tendon differentiation may be determined in tissue culture by investigating the ability of the bone composition of the present invention to differentiate or induce osteoblast phenotype, chondrocyte phenotype, ligament/tendon cell phenotype in cultured cells, such as primary cells, cell lines, or explants. For example, the cells may display increased production of a marker characteristic of osteoblasts and/or chondrocytes, such as alkaline phosphatase, etc. For example, the osteoinductive, chondroinductive, ligament/tendon differentiation potentials of the bone composition described herein may be more than 0.2, 0.4, 0.6, 0.8, 1, 2, 3, 4, 5, 6, 7, 8, 9 or 10 times greater than the control compositions and/or implants. In another example, the osteoinductive, chondroinductive, ligament/tendon differentiation potentials of the culture on the composition and/or implant described herein may be more than 10, 20, 30, 40, 50, 60, 70, 80, 90, 100, 500 or even 1000 times greater than those of the control composition and/or implant.

Osteoinductivity, chondroinductivity, ligament/tendon differentiation, for assessing the bone, cartilage, ligament or tendon forming potential induced by the bone composition and/or implant of the present invention in a location such as muscle, may also be evaluated using a suitable animal model. For example, intramuscular implantation into a rodent biceps femoris has been used as a model to assess osteoinductive activity of bioactive factors.

The invention also relates to methods of promoting cell attachment, proliferation or maintaining the differentiated state or preventing de-differentiation of osteoblasts, chondrocytes, ligament cells, tendon cells and/or any cell type disclosed herein with the methods comprising culturing the cells on a bone composition described herein. The proliferative activity of the bone composition may or may not be altered, including but not limited to, enhanced activity, relative to other compositions without the properties, e.g. the dimensions and L:W rations of the microfibers, described herein.

Mitogenicity may be assessed by investigating cell proliferation induced by the bone composition and/or implant of the present invention using various in vitro assays that measure metabolic activity, such as MTT [3-(4,5-dimethylthiazol-2-yl)-2,5-diphenyltetrazolium bromide] assay, alamarBlue® assay, and others. The alamarBlue® assay uses a non-cytotoxic reduction-oxidation indicator to measure cell metabolic activity, making it a nondestructive assay for assessing the mitogenic activity of the bone composition and/or implant described herein. Proliferation may also be assessed by measuring DNA quantification, such as by using a PicoGreen™ DNA assay, radioactive labeling of DNA synthesis, such as [3H]thymidine labeling or BrdU incorporation. Proliferation may also be assessed via manual cell counting, such as using a trypan blue hemacytometer.

The invention also relates to methods of increasing or promoting osteogenesis, chondrogenesis, or ligament/tendon genesis in cells. The methods may comprise culturing the cells on a bone composition described herein. As used herein, "osteogenesis" is the deposition new bone material or formation of new bone, including, but not limited to, intramembranous osteogenesis and endochondral osteogenesis. As used herein, "chondrogenesis" is the deposition new cartilage material or formation of new cartilage. As used herein, "ligament/tendon genesis" is the deposition new ligament and/or tendon material or formation of new ligament and/or tendon. The osteogenic, chondrogenic, ligament, or tendon inducing activity of the bone composition may or may not be altered, including but not limited to, enhanced activity, relative to other compositions without the properties, e.g. the dimensions and L:W rations of the microfibers, described herein. The cells may include cells in any tissue in which bone, cartilage, ligament, or tendon formation is desired, such as, but not limited to, bone, cartilage, ligament, muscle, tendon, etc.

The invention also relates to methods of treating a tissue or organ defect or injury, for example, a musculoskeletal, dental or soft-tissue defect or injury, in an animal comprising administering (1) cells cultured on the bone composition described herein and/or (2) the bone implant described herein to the tissue or organ defect (e.g. osseous defects, defects in cartilage, ligament, tendon, spinal disk, and tendon insertion site to bone).

The invention further relates to methods of treating a tissue or an organ defect or injury, for example a musculoskeletal, dental or soft-tissue defect, in an animal by applying a bone composition and/or implant described herein to the defect, and application to the defect may be accomplished by injecting the bone composition and/or implant into the defect, inserting the composition and/or implant between tissue or organ, or placing the bone composition and/or implant on top of the defect. The present invention is also directed to treating a defect or injury in an organ by applying a bone composition and/or implant to the defect.

In some embodiments, the cells described herein are progenitor cells or adult (or somatic) stem cells. In additional embodiments, the progenitor cells or the adult stem cells are derived from placenta, bone marrow, adipose tissue, blood vessel, amniotic fluid, synovial fluid, synovial membrane, pericardium, periosteum, dura, peripheral blood, umbilical blood, menstrual blood, baby teeth, nucleus pulposus, brain, skin, hair follicle, intestinal crypt, neural tissue, or muscle, or differentiated from a pluripotent cell type (embryonic stem cell, induced pluripotent stem cell) into a somatic stem cell type such as those from the aforementioned sources, or with cells coursed from transdifferentiated or directly differentiated cells, such as by way of converting a fibroblast directly to a mesenchymal stem cell or to a somatic cell such as an osteoblast.

EXAMPLES

Example 1

Debrided cortical bone was cut into fibers of 1.5 cm×2 mm×1 mm dimensions using Computer Numerical Control (CNC) machining. The fibers were treated by Allowash® to remove cellular components, fats, oils, and other soft tissues according to the manufacturer's suggested protocol. Then, the fibers were treated by PAD™ processing from Lifenet Health, Inc., Virginia Beach, Va., wherein a series of pulsatile hydrochloric acid treatments are used to remove the minerals from the cortical bone fibers, leaving behind collagen matrix and the endogenous proteins. The fibers were rinsed in buffer and water to remove the residual acid, and were buffered to a neutral pH range (around pH 7). The fibers were loaded into a mold of a predetermined shape. Pressure of 6.227 MPa (around 903 psi) was applied to the fibers in the mold for 30 minutes. Pressed fibers were frozen, and the frozen pressed fibers were lyophilized and retained the predetermined shape after lyophilization. Changes in the dimension, weight and volume after 30 minute incubation in a fluid are shown in Table 1 below. The pressed fibers were also incubated in 37° C. saline, in which swelling and dissociation were observed after 5 minutes. After 18 hours, the pressed fibers in 37° C. saline were dissociated completely and no mechanical integrity could be observed.

TABLE 1

| Parameters | Fluid | Length Change (+%) | Width Change (+%) | Fluid Weight: Fiber Weight (g:g) | Volume of Fluid (cm³) |
|---|---|---|---|---|---|
| CNC 0.009 1¾ T @100 psi 20 min press | PBS 1× Blood | 16.82 8.61 | 18.10 18.33 | 7.54:1 4.93:1 | 8.22 4.84 |
| CNC 0.003 1¾ T @100 psi 20 min press | PBS 1× Blood | 29.57 14.84 | 23.48 14.08 | 4.39:1 3.08:1 | 4.83 3.26 |
| Shaver 1¾ T @100 psi 20 min press | PBS 1× Blood | 12.23 19.35 | 13.62 14.41 | 3.46:1 6.33:1 | 4.29 7.13 |
| CNC 0.009 20 T @55 psi 5 min press | PBS 1× Blood | 10.46 45.25 | 16.73 49.63 | 13.46:1 13.07:1 | 1.51 0.58 |
| CNC 0.009 1¾ T @100 psi 5 min press | PBS 1× Blood | 29.77 13.34 | 22.60 16.12 | 7.35:1 6.07:1 | 3.75 3.27 |
| CNC 0.003 20 T @55 psi 5 min press | PBS 1× Blood | 16.54 15.48 | N/A N/A | 1.44:1 2.37:1 | 0.36 1.16 |
| CNC 0.003 1¾ T @100 psi 5 min press | PBS 1× Blood | 17.24 10.38 | 23.32 10.05 | 5.68:1 4.16 | 5.68 2.04 |
| Shaver 1¾ T @100 psi 5 min press | PBS 1× Blood | 2.32 -1.36 | 48.09 9.24 | 4.52:1 4.23:1 | 2.69 3.81 |
| Shaver 20 T @55 psi 5 min press | PBS 1× Blood | 21.40 4.86 | 24.05 20.84 | 4.14:1 5.91:1 | 2.98 2.64 |

Example 2

Samples of demineralized bone fibers were made from CNC cutting from two different cutting programs (0.003" and 0.009" chiploads) and from a bone shaver machine ("shaver"). These fibers were placed in either a 1.75 Ton press (about 6.5 MPa, operated at full pressure, or about 900 psi on a 25 mm×100 mm surface), or a 20 Ton press used at half pressure (~10 Ton, about 37 MPa) to compressed fibers into the 25 mm×100 mm "bubblewrap" mold for either 5 or 20 minutes of pressure to produce the shapes shown. The samples created with the variable fiber sizes and variable pressure inputs were placed in either PBS or clotting cow blood for up to 30 minutes to determine the amount of swelling (length and width change) and the weight change in samples to determine the volume of liquid absorbed. The amount of swelling and the weight change were used to extrapolate the void volume of the sample (porosity or pore size). A trend of increased PBS vs blood absorption was seen in low pressure (e.g. about 900 psi) samples, while the converse is true for high pressure (e.g. about 5160 psi) samples. Samples generated at high pressure could not be handled (picked up as a solid piece with tweezers) when they are kept in either blood or saline as the product was pressed too thin at many places and thus fragile both dry and more so when they are wet. Nonetheless, the low pressure (e.g. about 900 psi) samples could be handled readily as wetted with blood, and could be handled with care in saline samples. All samples matched the starting sample weights.

Blood wetting for samples made with different pressures, about 900 psi, 450 psi, and 225 psi, were compared. Moreover, grafts made at 900 psi but with 1/16" holes drilled through each of the "domes/bubbles" in the strip were compared to grafts made with preservon added while filling the mold (1 ml/g tissue). While no visible difference was observed for the blood wetting on the samples made with different pressures, the drilled graft and the preservon graft showed improved (i.e. reduced) contact angles for the applied blood (i.e. about 2 cc) as placed on the 25×25 mm pressed fiber strip sections. Moreover, a strip made with preservon had apparent higher flexibility in the dry state.

Figure 13A:
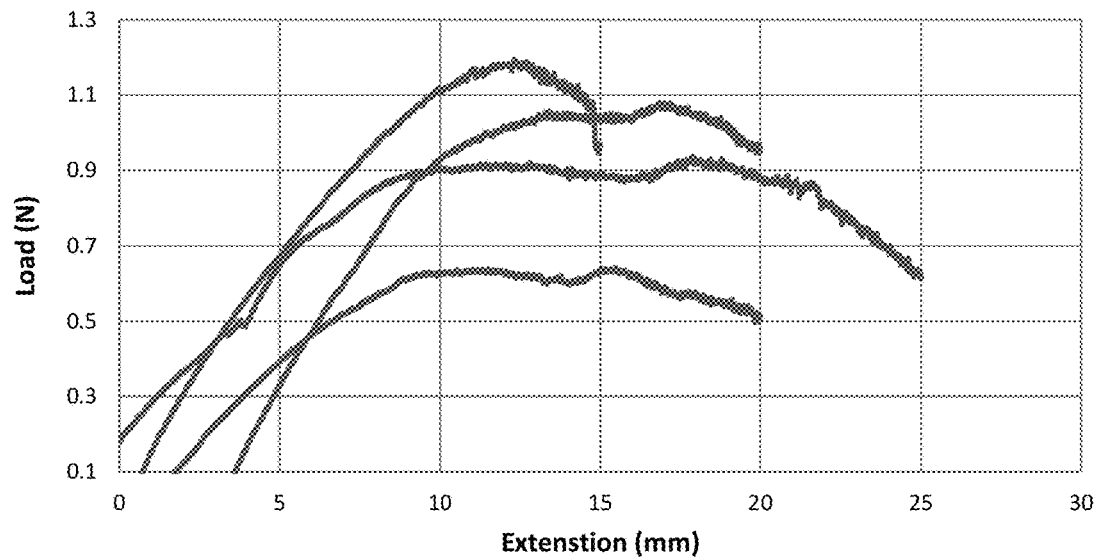
FIG. 13A shows three point bend mechanical testing data.

Three point bend mechanical testing (ASTM D790) was performed on the above bubblewrap-shaped 0.009" samples pressed in the 1.75 Ton press in a dry state prior to the incubation in any fluid. The results of this testing is shown in Table 2 below and FIG. 13A.

TABLE 2

| | Maximum Flexure stress (MPa) | Maximum Flexure Strain (%) | Flexure Extension at Maximum Flexure Stress (mm) | Energy at Maximum Flexure Stress (J) |
|---|---|---|---|---|
| Mean | 0.17 | 28.24 | 15.14772 | 0.00992 |
| Standard Deviation | 0.04157 | 9.04581 | 3.16062 | 0.00262 |
| Minimum | 0.12 | 17.08 | 12.35646 | 0.00691 |
| Maximum | 0.21 | 36.74 | 19.66009 | 0.01314 |
| Range | 0.09 | 19.66 | 7.30362 | 0.00623 |

Figure 13B:
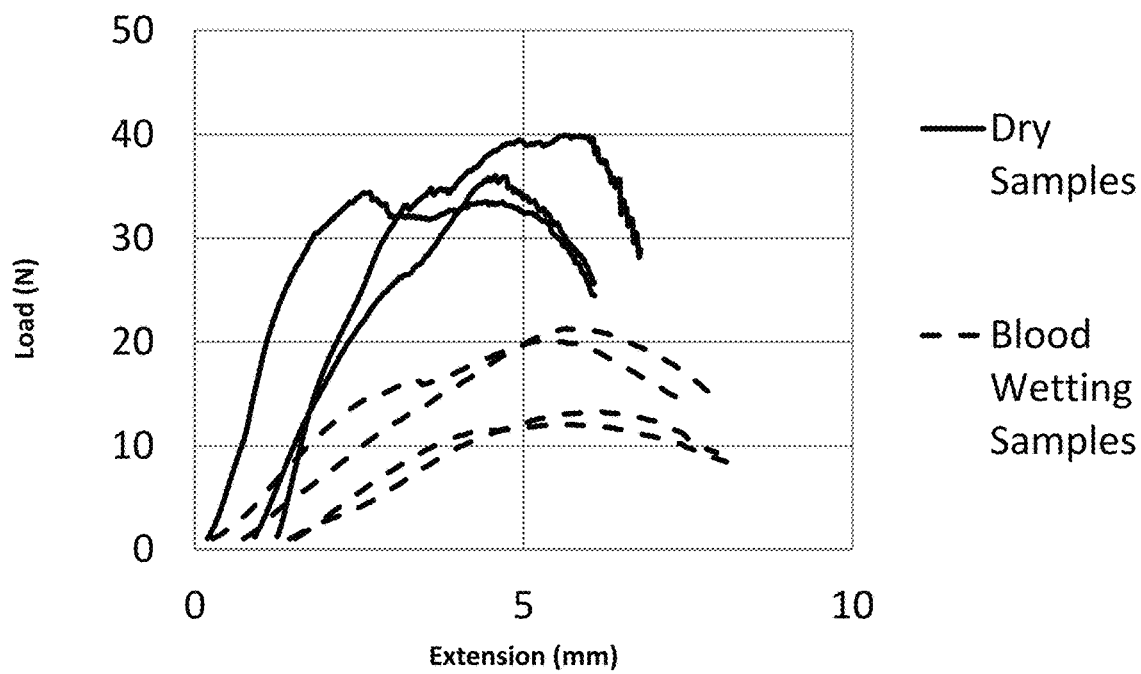
FIG. 13B shows 10 mm ball burst mechanical testing data.

10 mm Ball Burst Mechanical Testing was performed on the above bubblewrap-shaped 0.009" samples pressed in the 1.75 Ton press in a dry state prior to the incubation in any fluid and in a wet state after the incubation in blood. The experimental protocol according to ASTM D3787 (astm.org/Standards/D3787.htm) modified with 10 mm ball, instead of 245 mm ball was used. The results of this testing is shown in Tables 3 and 4 below and FIG. 13B.

TABLE 3

Ball Burst Mechanical Testing of Dry Samples

| | Maximum Load (N) | Normalized Load | Maximum Slope (Automatic) (N/mm) | Extension at Max Load (mm) |
|---|---|---|---|---|
| Mean | 36.81 | 41.82682 | 21.21321 | -4.28 |
| Standard Deviation | 2.84769 | 3.23601 | 5.49289 | 1.4922 |
| Coefficient of Variation | 7.73669 | 7.73669 | 25.89373 | -34.8424 |
| Minimum | 34.42 | 39.11613 | 14.89845 | -5.61 |
| Maximum | 39.96 | 45.40948 | 24.8851 | -2.67 |
| Range | 5.54 | 6.29334 | 9.98665 | 2.94 |

TABLE 4

Ball Burst Mechanical Testing of Wet Samples

| | Maximum Load (N) | Normalized Load | Maximum Slope (Automatic) (N/mm) | Extension at Max Load (mm) |
|---|---|---|---|---|
| Mean | 16.69 | 18.97064 | 5.18065 | -5.71 |
| Standard Deviation | 4.67489 | 5.31237 | 1.24254 | 0.32213 |
| Coefficient of Variation | 28.00313 | 28.00313 | 23.98425 | -5.64173 |
| Minimum | 12.08 | 13.7269 | 4.02093 | -6.12 |
| Maximum | 21.29 | 24.19875 | 6.92772 | -5.33 |
| Range | 9.22 | 10.47185 | 2.90679 | 0.78 |

Example 3

Bone fibers from CNC and shaver cuts pressed into binder-free shapes were placed into a lumbar spine in a cadaver and hydrated with saline for 10 minutes. The surrounding soft tissue was replaced, and the tissue was massaged to simulate normal closure. The result showed that the fibers shapes maintained their general shapes and surface topology in this implantation model. The fibers were further found to conform to the defect space and migrate into the interverterbral spaces which increase native bone-to-implant contact as to enhance bone fusion.

Example 4

The polymer (Polycaprolactone or Polydioxanone) was dissolved in chloroform or hexafluoroisopropanol at 0.1 mg/ml and added to bone fibers from Example 1 in 1:1 ratio (dry weight bone:dry weight polymer). The volatile solvents were allowed to evaporate in a fume hood to leave a polymer coating upon the bone fibers. Polymer coated bone fibers were then compressed at 6.5 MPa for a period from 30 min to 1 hour.

Example 5

Figure 5:
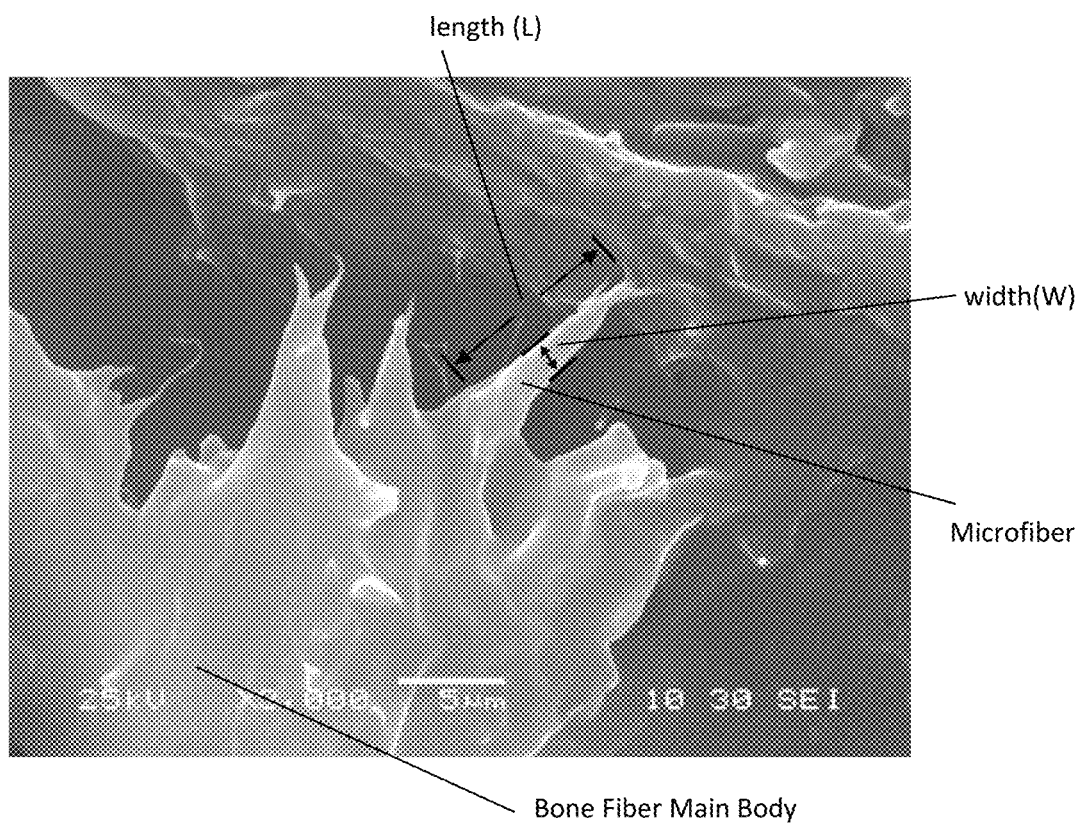
FIG. 5 shows the SEM image of a dry bone fiber sample according to some embodiments of the present invention, illustrating the bone fiber main bodies and microfibers.

Scanning electron microscope (SEM) provides a tool for the study and characterization of bone compositions. FIG. 5 illustrates SEM images of sample bone fibers cut with CNC (CNC 0.003 and CNC 0.009 with a 0.003" and 0.009" chipload on the cutter, respectively) of the present invention. The images were acquired after dry bone fibers were wetted in saline for 30 minutes. SEM images of different magnifications may be used for the measurement of bone fiber dimensions, e.g. width and length.

Figure 3A:
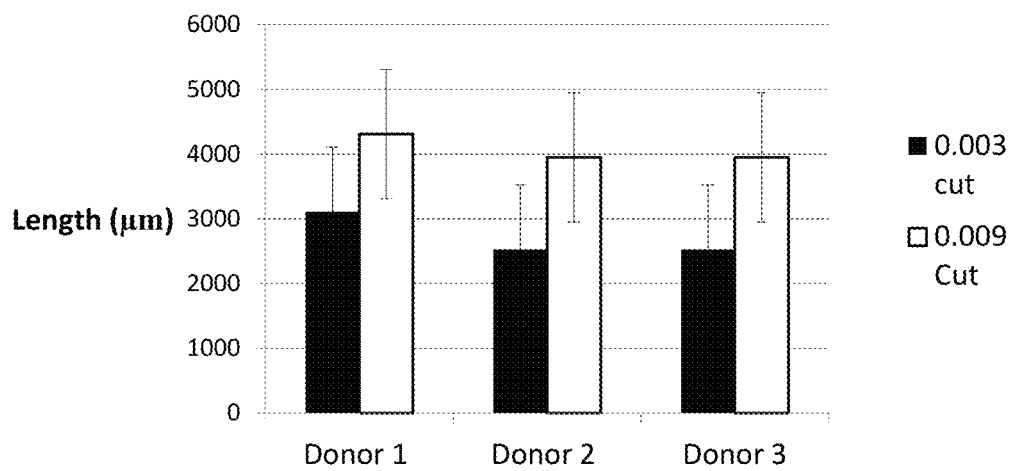
FIGS. 3A and 3B show the average length and width of bone fibers cut by Computer Numerical Control (CNC) between each donor according to some embodiments of the present invention.
Figure 3B:
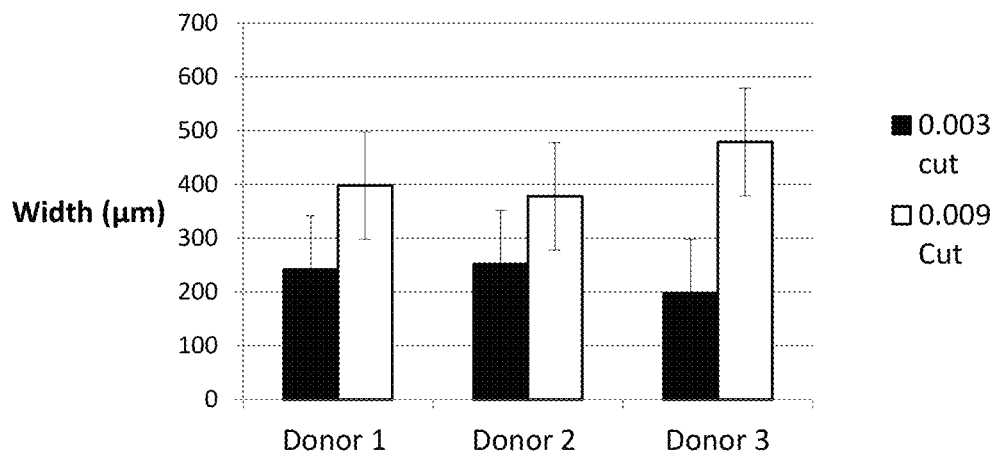

FIGS. 3A and 3B show the average length and width of bone fibers cut with CNC from three different donors as measured by SEM with a reference scale bar using ImageJ64 (NIH Shareware) according to some embodiments of the present invention.

DBM fibers made by CNC cutting (with a 0.003" and 0.009" chipload on the cutter) were processed by Allowash and demineralization (PAD processing) and lyophilized. The fibers were mounted dry on carbon tape and sputter coated with gold by plasma deposition. The coated fibers were imaged by scanning electron microscopy at Jefferson Labs (Newport News, VA) using a JOEL JSM-6060LV. The fiber images with scale bar for reference were measured with ImageJ64 (NIH shareware) to determine the average length and width of the fibers using 30 unique fibers and statistically averaged in ImageJ64.

Table 5 shows the dimensions (average length, average width, length range, and width range) of the bone fibers cut with CNC derived from SEM images with the fibers measured and dimensions averaged by ImageJ64. The bone fibers were from three (3) donors and n=30 from each donor for the bone fiber samples.

TABLE 5

| Sample | Average Length ± SD | Length Range | Average Width ± SD | Width Range |
|---|---|---|---|---|
| CNC 0.003 | 2854 ± 1146 μm | 743-5716 μm | 230 ± 124 μm | 24-601 μm |
| CNC 0.009 | 3818 ± 1753 μm | 987-8250 μm | 418 ± 217 μm | 75-1258 μm |

Example 6

Figure 4:
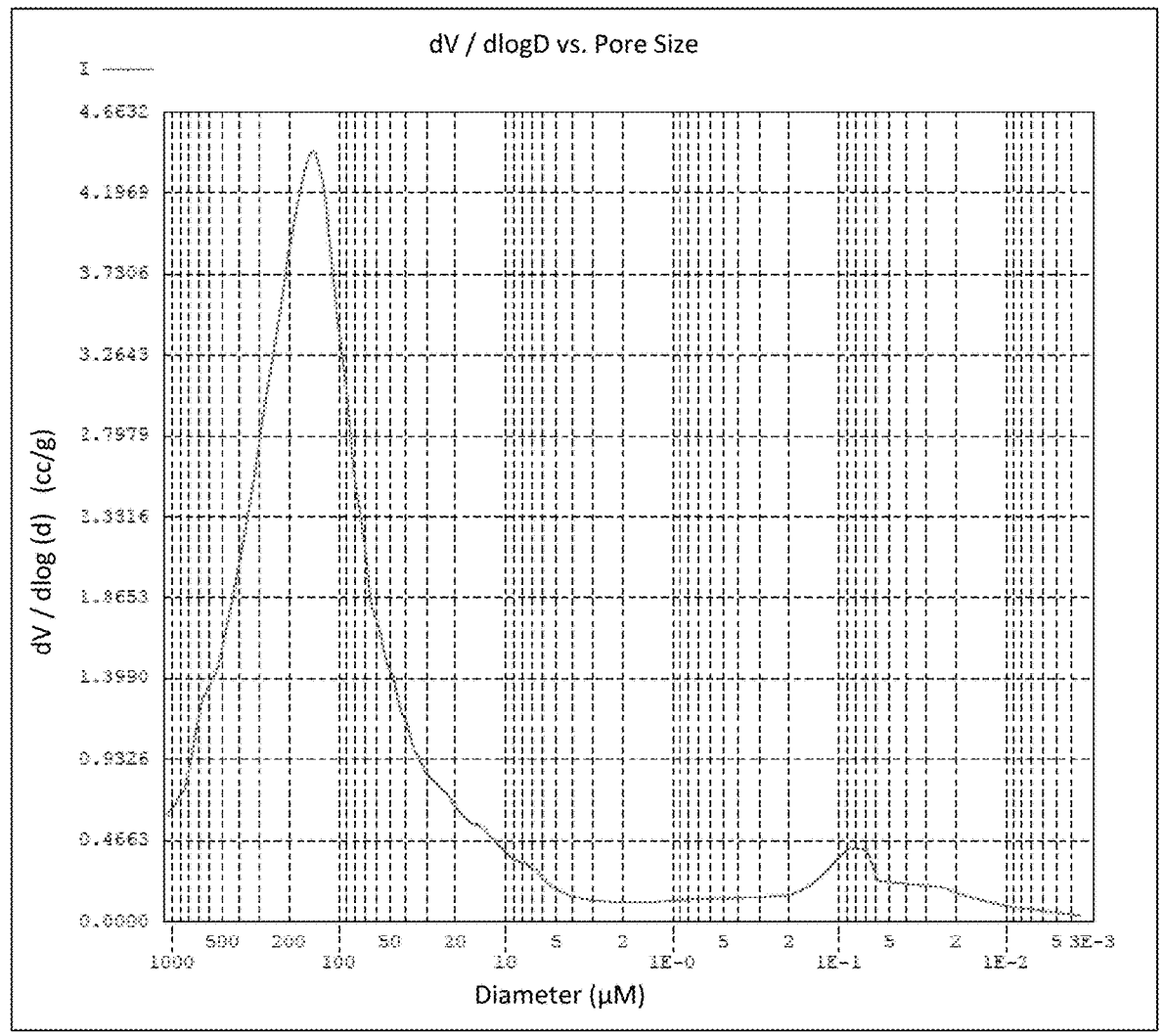
FIG. 4 shows the pore distribution of wetted bone fiber samples made from bone fibers cut with CNC via mercury porosimetry according to some embodiments of the present invention.

The bubblewrap-shaped 0.009" samples pressed in the 1.75 Ton press in a wet state after the incubation in PBS according to Example 2 above was prepared and pore size distribution of the sample was measured. FIG. 4 shows the pore size distribution of wet CNC 0.009 bone fiber sample via mercury porosimetry according to some embodiments of the present invention where the graft is represented at equilibrium after wetting and expanded for 30 minutes.

Compressed bone fibers (both CNC and Shaver) were allowashed, demineralized (by PAD) and compressed into bubble wrap molds. Compressed fibers in molds were lyophilized to produce the DBM shaped fiber strips. The strips were cut into 1 cm×1 cm sections and analyzed in triplicate for each group by mercury intrusion and extrusion porosimetry to determine pore volume and size distribution, the total surface area, mean media and modal pore size, cumulative and differential pore volume and area distribution.

Table 6 shows a summary of pore sizes for dry and wet bone compositions in the bubblewrap-shaped samples.

TABLE 6

| Sample | Dry Avg. Pore Size (mode) | Dry Avg. Pore Size (mean) | Wet 5 min Avg. Pore Size (mode) | Wet 5 min Avg. Pore Size (mean) | Wet 30 min Avg. Pore Size (mode) | Wet 30 min Avg. Pore Size (mean) | Wet 30 min Pore Size Range |
|---|---|---|---|---|---|---|---|
| CNC 0.003 | 57 μM | 50 μM | 28 μM | 27 μM | 31 μM | 26 μM | 0.003-1073 μM |
| CNC 0.009 | 54 μM | 40 μM | 205 μM | 70 μM | 158 μM | 70 μM | 0.003-1055 μM |
| Shaver (BLX) DBM Fiber Strip | 87 μM | 45 μM | 301 μM | 60 μM | 295 μM & 0.9 μM * | 51 μM | 0.003-1059 μM |

* notable bimodal distribution.

Table 7 shows a summary of pore sizes for additional dry bone compositions in the bubblewrap-shaped 0.009" samples prepared with different pressure.

TABLE 7

| | PSI | Mean (micron) | Mode (micron) | Median (micron) | Pore diameter range (micron) |
|---|---|---|---|---|---|
| | 225 | 38.23 | 31.79 | 50.16 | 0.003585-1064.391846 |
| Sample A | 450 | 37.7 | 31.4 | 47.22 | 0.003585-1064.391846 |
| | 900 | 21.97 | 19.79 | 28.38 | 0.003587-1068.828857 |
| | 225 | 32.72 | 33.71 | 39.66 | 0.003577-1059.996582 |
| Sample B | 450 | 1.251 | 29.83 | 40.58 | 0.003572-1064.391846 |
| | 900 | 0.626 | 29.36 | 42.07 | 0.003581-1082.359253 |

The bone compositions made from bone fibers cut with CNC according to some embodiments of the present invention have a different average mode for pore size compared with the shaver fibers. In particular, the bone fibers cut with CNC do not show a notable bimodal distribution of mode for pore sizes after the dry fiber was wetted for 30 minutes.

Flat discs of the demineralized bone fibers (prepared by CNC 0.009" chipload) having 10 mm diameter were made by applying pressure from 225 psi to 14,000 psi (i.e. 225, 450, 900, 1800, 3600 and 14000 psi) were prepared, and the pore size of the dry discs were measured by mercury porosimetry. The porosity measured is shown in Table 8 below.

TABLE 8

| | PSI | Mode (microns) | Pore diameter range (microns) |
|---|---|---|---|
| Sample A | 225 | 18.43 | 0.003577-1068.828857 |
| | 450 | 17.54 | 0.003588-1064.391846 |
| | 900 | 18.09 | 0.003588-1073.302979 |
| | 1800 | 23.53 | 0.007639-1051.309204 |
| | 3600 | 21.54 | 0.003582-1059.996582 |
| | 14000 | 19.18 | 0.003587-1064.391846 |
| Sample B | 225 | 20.43 | 0.003583-1073.302979 |
| | 450 | 16.88 | 0.003581-1068.828857 |
| | 900 | 18.14 | 0.003574-1068.828857 |
| | 1800 | 18.28 | 0.003584-1073.302979 |
| | 3600 | 23.98 | 0.003587-1068.828857 |
| | 14000 | 19.36 | 0.003589-1073.302979 |

Flat discs of the demineralized bone fibers (prepared by CNC 0.009" chipload) having 10 mm diameter were made by applying pressure from 225 psi to 14,000 psi (i.e. 225, 450, 900, 1800, 3600 and 14000 psi), were kept in PBS for 30 minutes, frozen and lyophilized. The shapes of the discs were maintained for the discs made with pressures at 900 psi or less, and the pore sizes were measured as shown in Table 9 below. On the other hand, the discs made with pressures at 1800 or above lost mechanical integrity after wetting and could not be tested for wet compressive strength or porosity by mercury porosimetry.

TABLE 9

| | PSI | Mode (microns) | Pore diameter range (microns) |
|---|---|---|---|
| Sample A | 450 | 50.73 | 0.003577-1077.809448 |
| | 900 | 102.3 | 0.003574-1064.391846 |

TABLE 9-continued

| | PSI | Mode (microns) | Pore diameter range (microns) |
|---|---|---|---|
| Sample B | 450 | 90.64 | 0.003578-1068.828857 |
| | 900 | 104.6 | 0.003591-1068.828857 |

Example 7

FIG. 5 shows an SEM image of a dry bone fiber sample, illustrating the bone fiber main body and microfibers. The length and width of a sample microfiber are identified.

Figure 6:
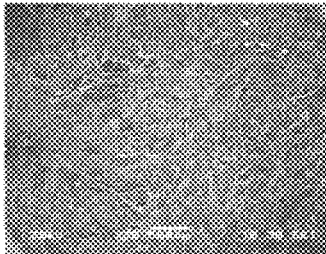
FIG. 6 illustrates SEM images of samples of dry bone fibers in different magnifications (mag.) according to some embodiments of the present invention.
Figure 6:
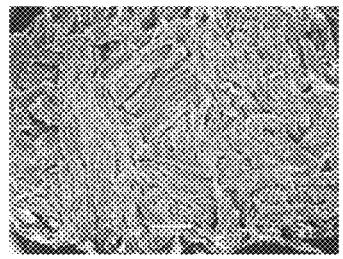
Figure 6:
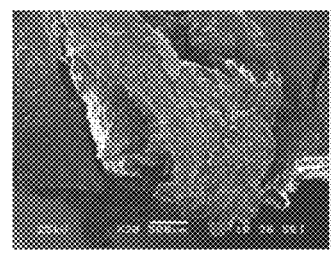
Figure 6:
Figure 6:
Figure 6:
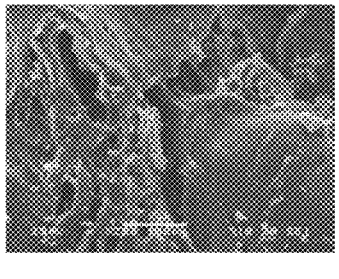
Figure 6:
Figure 6:
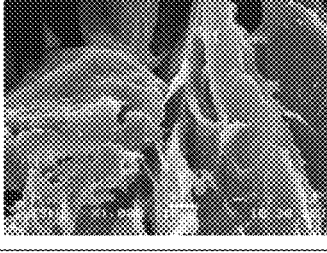
Figure 6:
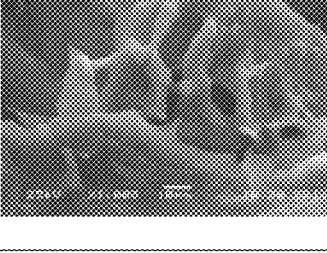
Figure 6:
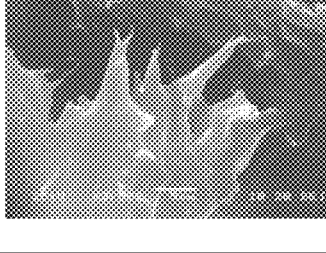
Figure 6:
Figure 6:
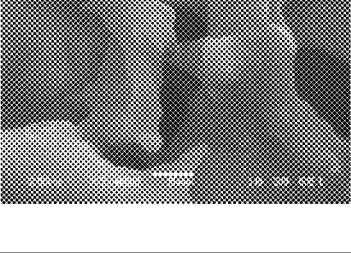

As shown in FIG. 6, samples of dry bone fibers are visualized and recorded in different magnifications (mag.) with SEM.

Compressed DBM fibers (both CNC at 0.003" and 0.009" chipload and as cut by a bone Shaver) were allowashed, demineralized (PAD) and compressed into bubble wrap molds. Compressed fibers were lyophilized to produce the DBM shaped fiber strips. Compressed DBM fibers strips (~1 cm×1 cm) were mounted dry with carbon tape on a stub and sputter coated with gold by plasma deposition. The coated fibers were imaged by SEM at Jefferson Labs (Newport News, Va.) using a JOEL JSM-6060LV, with different magnifications.

The microfibers were more identifiable in the images with 1,000 and 3,000 times magnification, as demonstrated in FIG. 5 with 3000 times magnification.

Using representative scanning electron microscope images, the average length (L) and width (W) of the microfibers seen projecting off of the approximated main fiber body on the CNC cut (CNC 0.003 and CNC 0.009) and bone shaver cut demineralized bone fibers (Shaver) were measured (n=20 points) by ImageJ64 (NIH shareware). The average length (L), width (W) and respective ranges are shown, with the length-to-width (L:W) ratio calculated. The resulting average microfiber dimensions are shown in Table 10.

TABLE 10

| Sample | Average Length (L) | Length Range | Average Width (W) | Width Range | Average L:W Ratio |
|---|---|---|---|---|---|
| CNC 0.003 | 6.853 ± 3.015 μm | 2.909-10.717 μm | 1.346 ± 0.582 μm | 0.434-2.330 μm | 5.092 |
| CNC 0.009 | 6.414 ± 5.016 μm | 2.976-16.141 μm | 0.849 ± 0.467 μm | 0.239-1.660 μm | 7.555 |
| Shaver | 12.302 ± 11.717 μm | 4.310-38.570 μm | 5.989 ± 4.994 μm | 2.915-18.790 μm | 2.054 |

Figure 7:
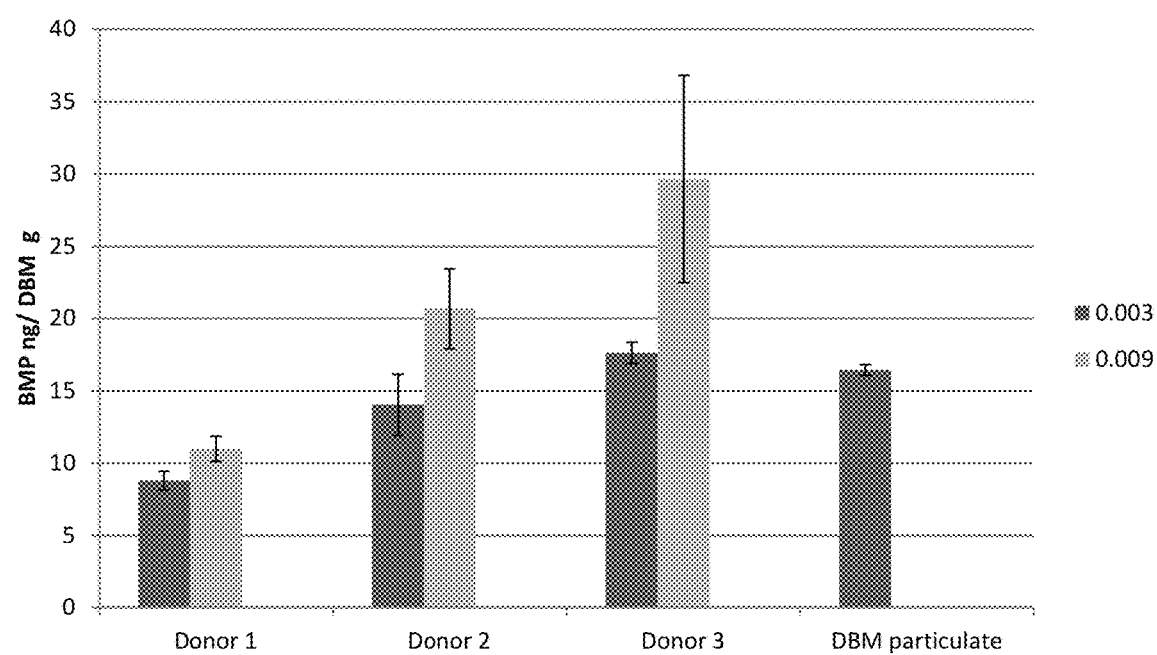
FIG. 7 shows the amounts of BMP-2 growth factor in bone composition samples prepared by CNC 0.003 and 0.009.

R&D systems Quantakine kit for BMP-2 was used to measure the amount of BMP in the bone composition samples. The samples of the 0.003" and 0.009" cut fibers and comparative DBM particulate from 3 donors were digested overnight in collagenase and added to the plate according to the manufacturer's instructions. Results, as shown in FIG. 7, demonstrated that the 0.009" cut fibers preserve more BMP-2 compared to the 0.003" cut fibers after demineralization process.

Example 8

Figure 8:
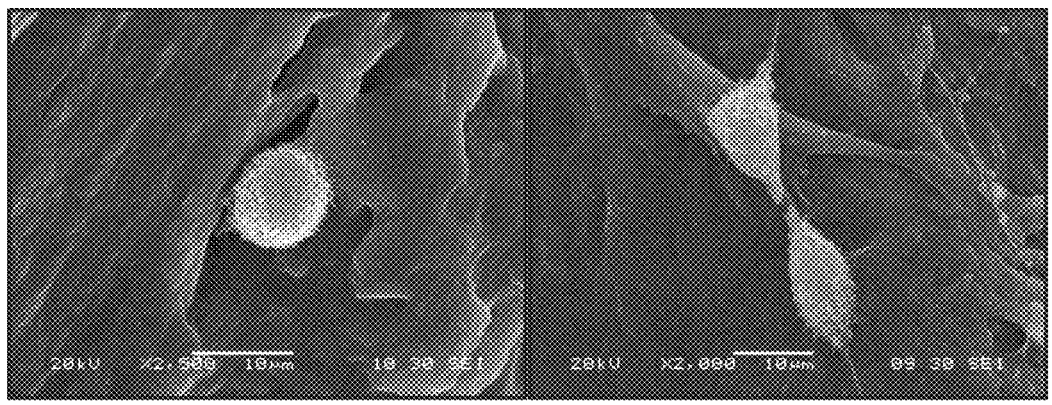
FIG. 8 shows sample SEM images of bone marrow-derived mesenchymal stem cells (BMSCs) growing on bone implants from demineralized bone matrix (DBM) fibers according to some embodiments of the present invention.

FIG. 8 shows sample SEM images of bone marrow stem cells (BMSCs) on bone implants from DBM fibers (CNC 0.009) after a day or week of culture.

200,000 bone marrow derived mesenchymal stem cells were cultured on compressed bone fibers (CNC 0.009) in xeno-free, serum-free StemPro (Invitrogen) for up to 7 days. The fibers with the cells were fixed at day one and say seven in glutaraldehyde in cacodylate buffer and then dehydrated with osmium tetroxide. DBM fibers strips (~1 cm×1 cm) were mounted dry on a carbon tape on a stub and sputter coated with gold by plasma deposition. The coated fibers were imaged with SEM at Jefferson Labs (Newport News, Va.) using a JOEL JSM-6060LV. The image of the culture sample after 7 days of culture shows that the cells were spread across DBM fibers (and apparently undergoing mitosis).

Figure 9:
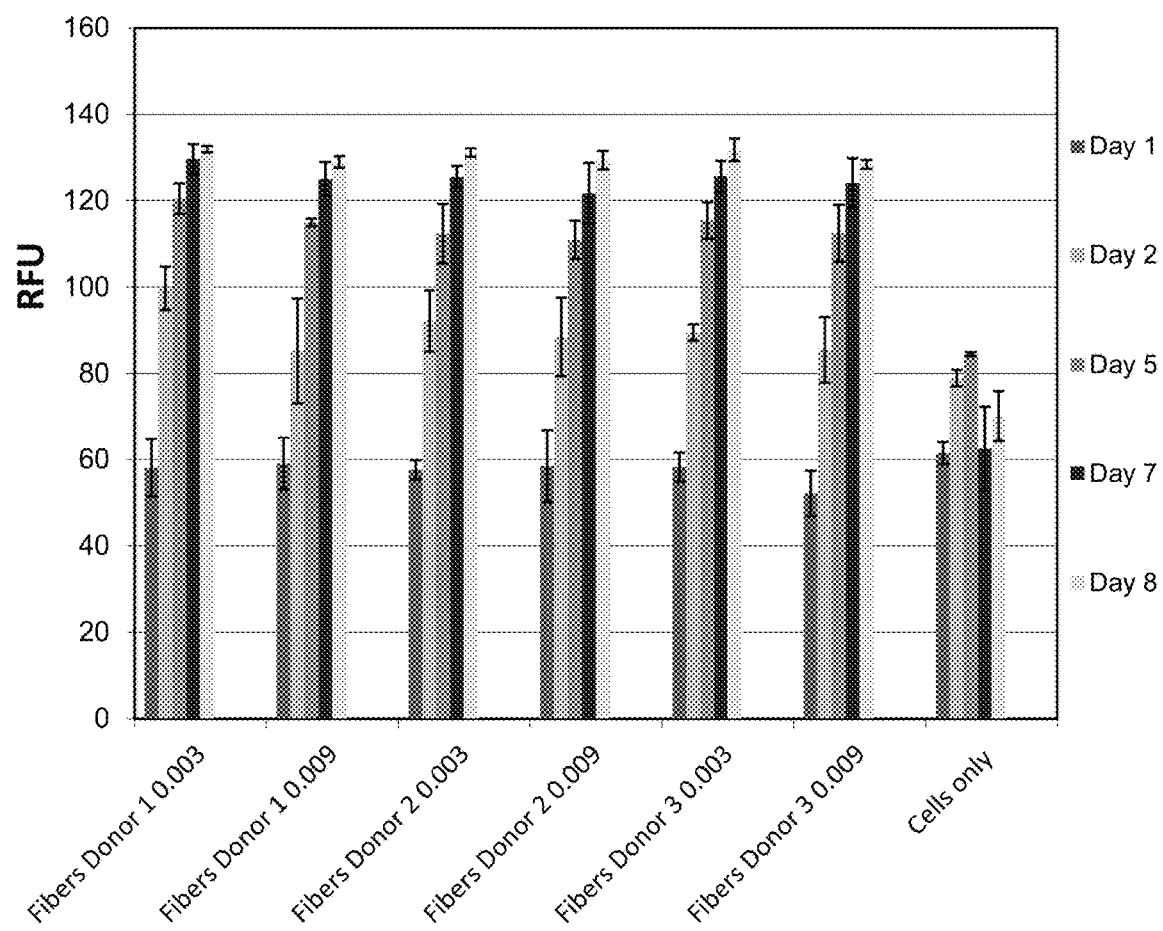
FIG. 9 illustrates BMSC growth on implants from bone fibers according to some embodiments of the present invention.

FIG. 9 illustrates BMSC growth on bone fiber where the growth is shown with relative florescence units (RFU) by an AlamarBlue assay. 100,000 bone marrow derived mesenchymal stem cells (BMSCs) were seeded upon a 48 well tissue culture plate coated on the bottom with weight-matched DBM fibers from 3 different donors (prepared from using 0.003" or 0.009" CNC chipload) and compared to cells grown alone without bone fibers on tissue culture plastic (BMSCs only group). AlamarBlue dye reagent was added to the media daily and the media was collected and measured on a fluorescent plate reader to determine the relative fluorescent units from each well daily, corresponding to the cellular metabolic activity for each cell-substrate from 1 to 8 days of culture.

As shown by FIG. 9, the metabolic activity of the BMSCs was observed to increase daily on DBM fibers, suggesting lack of cytotoxicity from the fibers. BMSCs growing on bone fibers cut with CNC demonstrate enhanced cell growth.

Example 9

Figure 10:
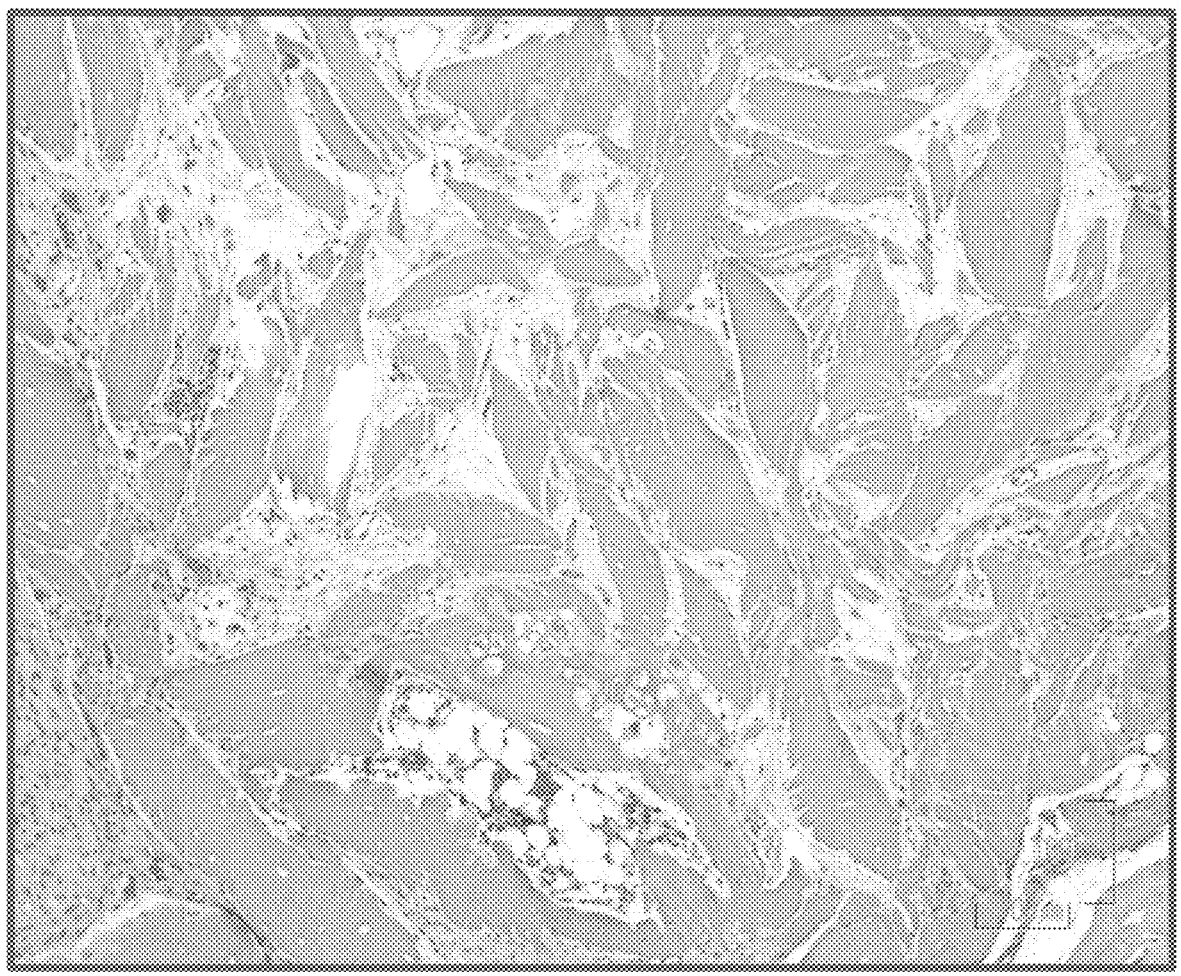
FIG. 10 illustrates in vivo bone fiber spacing, cellularity, and osteoblastogenic differentiation for a bone composition implant according to some embodiments of the present invention.

FIG. 10 illustrates an image of an exemplary bone composition implant, showing in vivo bone fiber spacing and cellularity. Compressed fibers from 3 unique donors were processed into DBM fibers with either a 0.003" or 0.009" CNC chipload. The two fiber groups pressed into strips were sectioned to 25 mg samples, terminally sterilized, and then implanted into athymic mice (n=4 implants per donor for a total of 12 implants per CNC group) and compared to non-pressed fibers from different CNC cut fiber geometries. The implants were explanted after 4 weeks in life and prepared for H&E histology to assess new bone element formation induced by the implants. Cellularity seen around all fibers suggested fiber spacing to be suitable for cell infiltration. The image shows the results of Hematoxylin and Eosin (H&E) staining of an explanted shaped DBM fibers along with the graft-induced new bone elements seen throughout the implants for the DBM fiber strip and loose fiber implants, with 12 separate sections scored by histopathology metrics per fiber group to give a percentage of each group showing new bone element formation.

Figure 11:
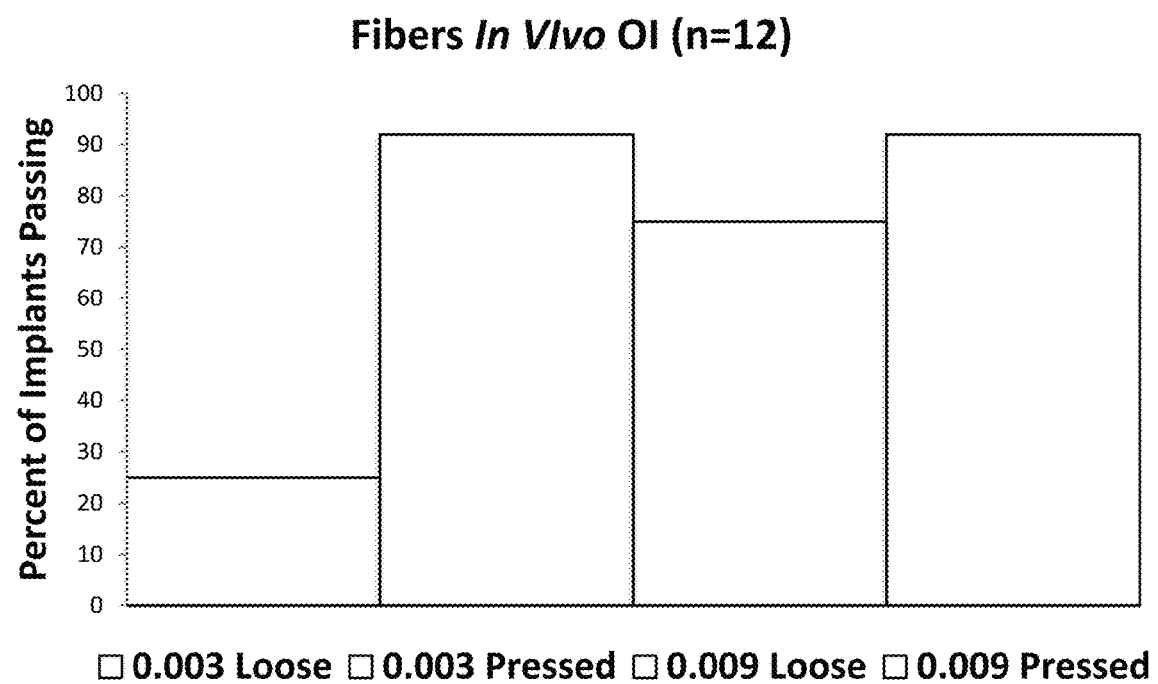
FIG. 11 demonstrates the percentage of implants passing osteoinductivity (OI) assays in vivo for bone implants and the relationship with fiber packing density (loose vs compressed) according to some embodiments of the present invention.

FIG. 11 demonstrates the percentage pass rate of osteoinductivity (OI) for bone implants and the relationship with fiber packing density. As shown in FIG. 10, pressing the CNC 0.003 fibers significantly enhances OI pass rate.

Example 10

Figure 12:
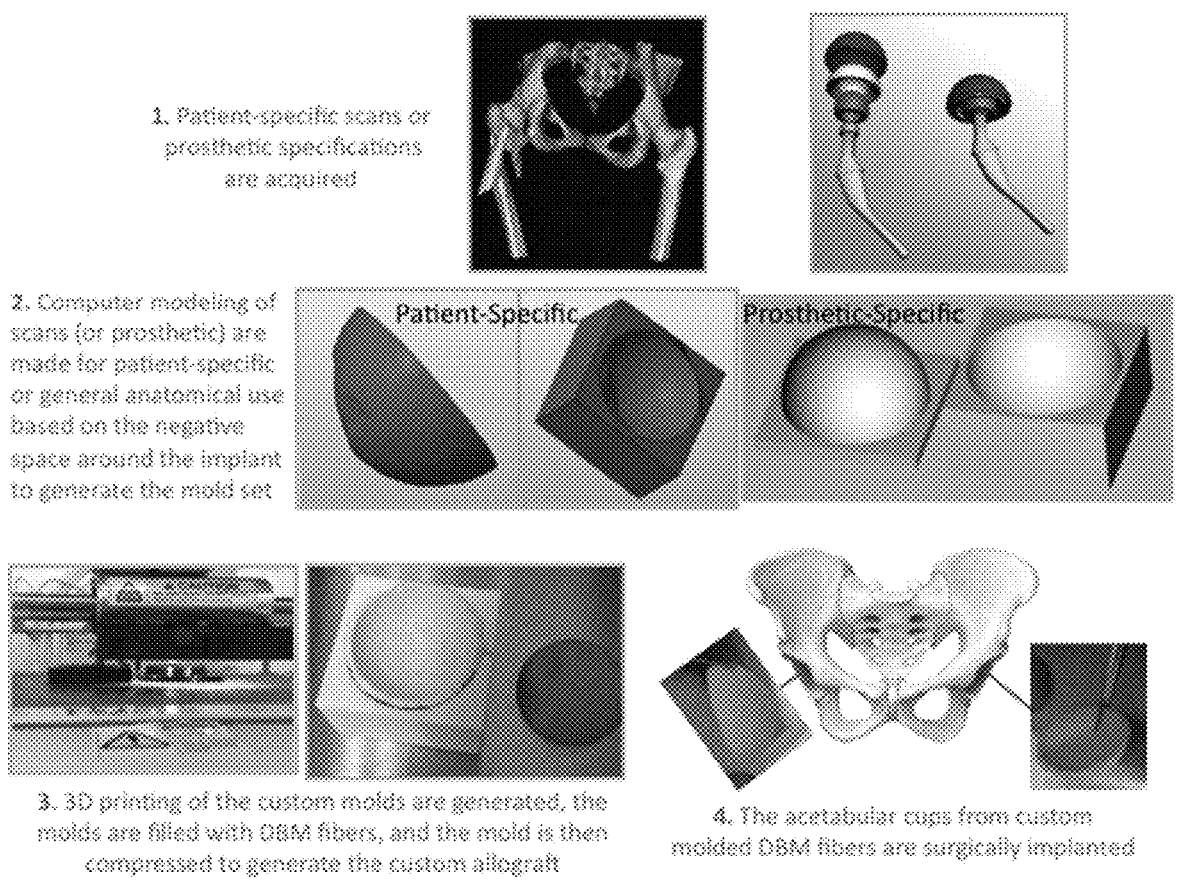
FIG. 12 shows the process of designing and molding a bone implant according to some embodiments of the present invention.

FIG. 12 shows the process of designing and molding a bone implant (bone fiber graft) according to some embodiments of the present invention.

The mold comprises a 3D printed base plate with a concave facet and a core block with a convex facet. The mold is produced by 3D printing based on the 3D computer imaging (computed tomography) measures of an individual's bone structure adjacent to the acetabulum. The computer aided design (CAD) drawings of an implant anatomically match the patient bone for generating the molds required to product the custom cast shaped DBM fiber implant. This approach is in contract to the nonspecific compressed fiber strips. The process of the present invention allows any patient-specific hard tissue to be converted from a 3D medical image scan to a computer rendering, whereby the negative space around the rendering is used to design molds which may then be manufactured (additive or subtractive means) to rapidly produce a patient-matched DBM fiber implant to reduce surgical time. This approach is also proven for generating fiber shapes which mate with prosthetics, such as artificial hip implants

What is claimed is:

1. A bone composition comprising bone fibers, wherein the bone fibers comprise microfibers having an average length (L) and an average width (W), wherein the average L:W ratio is greater than about 2.

2. The bone composition of claim 1, wherein the average L:W ratio is greater than about 5.

3. The bone composition of claim 1, wherein the average L:W ratio is greater than about 7.

4. The bone composition of claim 1, wherein the average L:W ratio is in a range from 2 to 30.

5. The bone composition of claim 1, wherein the average L:W ratio is in a range from 5 to 8.

6. The bone composition of claim 1, wherein the W of the microfibers is less than about 2 µm.

7. The bone composition of claim 1, wherein the W of the microfibers is less than about 1 µm.

8. The bone composition of claim 1, wherein the L of the microfibers is less than about 12 µm.

9. The bone composition of claim 1, wherein the L of the microfibers is less than about 7 µm.

10. The bone composition of claim 1, wherein the bone composition is wet and the mode of the pore sizes of the wet bone composition is in a range from 25 to 250 µm.

11. The bone composition of claim 10, wherein the mode of pore sizes of the wet bone composition at equilibrium does not have a bimodal distribution.

12. The bone composition of claim 1, wherein when the bone composition is wet, the mean of the pore sizes of the wet bone composition is in a range from 20 to 100 µm.

13. The bone composition of claim 12, wherein the mean of pore sizes of the wet bone composition at equilibrium is less than 30 µm or more than 65 µm.

14. The bone composition according to claim 1, further comprising at least one cell and/or at least one bioactive factor.

15. The bone composition according to claim 1, wherein the bone composition comprises bone particles having a median diameter of about 10-1,000 microns, a median length of about 0.5-100 mm, and a median thickness of about 10-1000 microns.

16. The bone composition of claim 1, wherein the W of the microfibers is less than about 5 µm.

* * * * *